US012799091B2

(12) United States Patent
Tong

(10) Patent No.: US 12,799,091 B2
(45) Date of Patent: Nov. 17, 2026

(54) ANHYDROUS POLYMORPHS OF ANDROGEN RECEPTOR ANTAGONIST, PREPARATION METHOD THEREFOR, AND USE THEREOF

(71) Applicant: SUZHOU KINTOR PHARMACEUTICALS, INC., Suzhou (CN)

(72) Inventor: Youzhi Tong, Suzhou (CN)

(73) Assignee: SUZHOU KINTOR PHARMACEUTICALS, INC., Suzhou (CN)

( * ) Notice: Subject to any disclaimer, the term of this patent is extended or adjusted under 35 U.S.C. 154(b) by 439 days.

(21) Appl. No.: 18/551,444

(22) PCT Filed: Mar. 22, 2022

(86) PCT No.: PCT/CN2022/082274
§ 371 (c)(1),
(2) Date: Sep. 20, 2023

(87) PCT Pub. No.: WO2022/199577
PCT Pub. Date: Sep. 29, 2022

(65) Prior Publication Data
US 2024/0182442 A1 Jun. 6, 2024

(30) Foreign Application Priority Data
Mar. 23, 2021 (CN) ........................ 202110310216.8

(51) Int. Cl.

| | |
|---|---|
| ***C07D 401/04*** | (2006.01) |
| ***A61K 31/4439*** | (2006.01) |
| ***A61K 31/506*** | (2006.01) |
| ***A61K 31/519*** | (2006.01) |
| ***A61K 31/5575*** | (2006.01) |
| ***A61K 31/58*** | (2006.01) |
| ***A61K 38/48*** | (2006.01) |

(52) U.S. Cl.
CPC ........ *C07D 401/04* (2013.01); *A61K 31/4439* (2013.01); *A61K 31/506* (2013.01); *A61K 31/519* (2013.01); *A61K 31/5575* (2013.01); *A61K 31/58* (2013.01); *A61K 38/4893* (2013.01)

(58) Field of Classification Search
CPC .............. C07D 401/04; A61K 31/4439; A61K 31/506; A61K 31/519; A61K 31/5575; A61K 31/58; A61K 38/4893; A61K 45/06; A61P 15/00; A61P 17/00; A61P 17/10; A61P 17/14; A61P 35/00; C07B 2200/13
USPC ........................................................ 514/341
See application file for complete search history.

(56) References Cited

U.S. PATENT DOCUMENTS

| | | | | |
|---|---|---|---|---|
| 8,809,550 B2 * | 8/2014 | Tong | A61P 43/00 548/319.5 |
| 2012/0172406 A1 | 7/2012 | Tong | |
| 2015/0210649 A1 * | 7/2015 | Dwivedi | C07D 233/86 548/321.1 |
| 2015/0239848 A1 * | 8/2015 | Peddy | H04W 4/10 548/321.1 |

FOREIGN PATENT DOCUMENTS

| | | |
|---|---|---|
| CN | 101817787 A | 9/2010 |
| CN | 102757389 A | 10/2012 |
| CN | 102757389 B | 7/2015 |
| CN | 106810542 A | 6/2017 |
| WO | WO 2011/029392 A1 | 3/2011 |

OTHER PUBLICATIONS

Hsu et al. Oncotarget, Apr. 30, 2014;5(8):2187-97, doi: 10.18632/oncotarget.1886, Minoxidil may suppress androgen receptor-related functions (Year: 2014).*
PCT International Search report issued in International Patent Application No. PCT/CN2022/082274, mailed Jun. 6, 2022.
Extended European Search Report issued in European Patent Application No. 22774233.5, dated Mar. 19, 2025.
Florence, A. J., "Polymorph screening in pharmaceutical development," *European Pharmaceutical Review,* 4 (2010): 1-14.

* cited by examiner

*Primary Examiner* — Jared Barsky
*Assistant Examiner* — Liyuan Mou
(74) *Attorney, Agent, or Firm* — pH IP Law

(57) ABSTRACT

The present invention belongs to the technical field of pharmaceutical crystal chemistry, and relates in particular to anhydrous polymorphs of an androgen receptor antagonist, a preparation method therefor, and a use thereof. In particular, the present invention provides four anhydrous polymorphs of a compound of formula I (having crystalline forms A, B, C, and D, respectively), a method for preparing each of said anhydrous polymorphs, pharmaceutical compositions comprising said anhydrous polymorphs, and uses thereof in the prevention, alleviation and/or treatment of diseases or disorders related to androgen receptor activity.

formula I

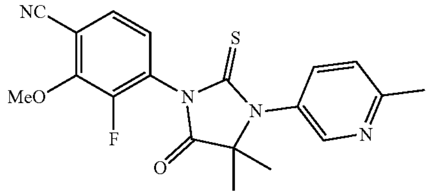

4 Claims, 7 Drawing Sheets

ANHYDROUS POLYMORPHS OF ANDROGEN RECEPTOR ANTAGONIST, PREPARATION METHOD THEREFOR, AND USE THEREOF

REFERENCES TO RELATED APPLICATIONS

This application is a U.S. National Stage application under 35 U.S.C. § 371 of International Application No. PCT/CN2022/082274, filed Mar. 22, 2022, which claims the priority of patent application No. 202110310216.8 titled "Anhydrous polymorphs of androgen receptor antagonist, preparation method therefor, and use thereof" filed in China on Mar. 23, 2021, the contents of which are incorporated herein by reference in its their entireties.

FIELD OF THE INVENTION

The present invention belongs to the technical field of pharmaceutical crystal chemistry and specifically relates to four anhydrous polymorphs of an androgen receptor antagonist, preparation methods of these polymorphs, and their uses in the pharmaceutical field.

BACKGROUND OF THE INVENTION

The same substance (a monomer or a compound) is likely to form a variety of crystals with completely different structure, morphology, and physical property under different conditions. This phenomenon is called crystal polymorphism, in which each crystal is also called polymorphy.

The crystal polymorphism is also relatively common in the pharmaceutical field. Under certain conditions, an active pharmaceutical ingredient can exist in a specific crystalline form, that is, form a specific polymorph. As different polymorphs of the same active pharmaceutical ingredient usually have different crystal structures, it may make the drug of crystalline form have different bioavailability, solubility, melting point, physical and chemical stability, etc., which in turn affects the safety and efficacy of the drug, etc., especially the physical and chemical stability is a prerequisite for determining whether a certain polymorph can be used as a pharmaceutical crystalline form.

The androgen receptor (AR) is a 110 kDa steroidal nuclear receptor and one of its key functions is androgen-activated gene transcription. The androgen receptor plays an important role in a variety of androgen-related diseases or conditions, such as prostate cancer, benign prostatic hyperplasia, androgenetic alopecia, muscle loss, acne, and hirsutism.

Chinese invention patent CN 102757389 B discloses a small molecule AR receptor antagonist (with a chemical name 4-[4,4-dimethyl-3-(6-methylpyridin-3-yl)-5-oxo-2-thioxoimidazolidin-1-yl]-3-fluoro-2-methoxybenzonitrile (shown in formula I) currently in the stage of clinical research), which is produced from intermediates 3a and 6e by microwave-assisted ring-forming reaction and purified by silica gel column chromatography, and is obtained in a basically colloidal or viscous state on a small test scale.

I

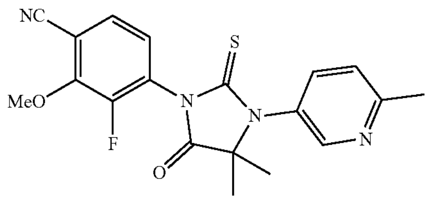

CONTENT OF THE PRESENT INVENTION

Problems to be Solved by the Invention

To ensure the physical and chemical stability of the drug during production and processing and storage of the drug, four different anhydrous polymorphs were obtained through in-depth study of the different aggregation states of the compound of formula I. All of them possess excellent physicochemical properties, such as crystallinity, solubility, hygroscopicity, chemical stability, and the stability of the crystalline form, and the corresponding preparation processes were operable, which provide a scientific basis for the clinical drug research.

Technical Solutions for Problem Solving

In a first aspect, the present invention provides an anhydrous polymorph of a compound of formula I.

formula I

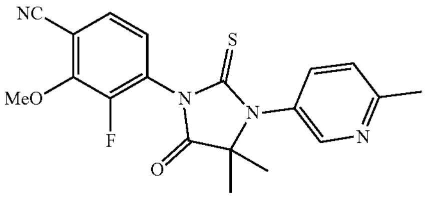

The anhydrous polymorph of a compound of formula I has a crystalline form D. The X-ray powder diffraction (XRPD) pattern of the crystalline form D comprises peaks at the following 2θ angles: 5.3±0.2°, 10.7±0.2°, 13.5±0.2°, 15.1±0.2° and 21.3±0.2°.

Further, the XRPD pattern of the crystalline form D comprises peaks at the following 2θ angles: 5.3±0.2°, 10.7±0.2°, 12.0±0.2°, 12.7±0.2°, 13.5±0.2°, 14.8±0.2°, 15.1±0.2°, 16.4±0.2°, 17.3±0.2°, 20.3±0.2°, 21.3±0.2°, 24.2±0.2° and 24.8±0.2°.

Further, the XRPD pattern of the crystalline form D comprises peaks at the following 2θ angles: 5.3±0.2°, 10.7±0.2°, 12.0±0.2°, 12.7±0.2°, 13.5±0.2°, 14.8±0.2°, 15.1±0.2°, 16.4±0.2°, 17.3±0.2°, 19.7±0.2°, 20.3±0.2, 21.3±0.2°, 22.5±0.2°, 23.1±0.2, 24.2±0.2°, 24.8±0.2°, 27.3±0.2°, 28.5±0.2°, 29.7±0.2° and 32.3±0.2°.

Further preferably, the XRPD pattern of the crystalline form D is substantially consistent with FIG. 1.

Further, the thermogravimetric analysis (TGA) profile of the crystalline form D shows a weight loss of about 1.6% at 150±1° C.

Preferably, the TGA profile of the crystalline form D is substantially consistent with FIG. 2.

Further, the differential scanning calorimetry (DSC) profile of the crystalline form D shows heat absorption at 167±1° C.

Preferably, the DSC profile of crystalline form D is substantially consistent with FIG. 2.

In a second aspect, the present invention provides a method for preparing an anhydrous polymorph of crystalline form D, which is selected from a slow volatilization method, a gas-solid diffusion method, a gas-liquid diffusion method, a polymer induction method, a grinding method and a suspension stirring method, preferably the suspension stirring method.

Preferably, the solvent used in the slow volatilization method is a volatile halogenated alkane or a straight-chain or branched C2-C6 nitrile; more preferably, the volatile halogenated alkane is methylene chloride or chloroform, and the straight-chain or branched C2-C6 nitrile is acetonitrile.

Preferably, the solvent used in the gas-solid diffusion method is a volatile alcohol or a volatile ether; more preferably, the volatile alcohol is methanol or ethanol, and the volatile ether is ethyl ether or methyl tert-butyl ether.

Preferably, the good solvent used in the gas-liquid diffusion method is a straight-chain or branched C2-C6 nitrile, preferably acetonitrile, and the antisolvent used is water; more preferably, the good solvent/antisolvent combination used in the gas-liquid diffusion method is acetonitrile/water.

Preferably, the good solvent used in the polymer induction method is a straight-chain or branched C2-C6 nitrile, preferably acetonitrile, and the polymer used is any one or more of polycaprolactone, polyethylene glycol, polymethyl methacrylate, sodium alginate, and hydroxyethyl cellulose, preferably an equal mass mixture.

Preferably, the grinding method process may be performed without solvent or with water as solvent.

Preferably, the solvent used in the suspension stirring method is water, alkane, alkyl alcohol, alkyl ketone, alkyl ester, chlorinated hydrocarbon, ether, aromatic hydrocarbon, straight-chain or branched C2-C6 nitrile, dimethyl sulfoxide, or chain or cyclic amide; more preferably, the alkane is n-heptane, pentane or n-hexane; the alkyl alcohol is methanol, ethanol or isopropanol: the alkyl ketone is acetone or methyl isobutyl ketone; the alkyl ester is ethyl acetate or isopropyl acetate; the chlorinated hydrocarbon is dichloromethane or chloroform; the ether is ethyl ether, methyl tert-butyl ether, 1,4-dioxane or 2-methyltetrahydrofuran; the aromatic hydrocarbon is benzene, toluene or xylene; the straight-chained or branched C2-C6 nitrile is acetonitrile: the amide in chain form is N,N-dimethyl formamide or N,N-dimethylacetamide, and the amide in cyclic form is N-methyl-2-pyrrolidone; Further preferably, the mixed solvent used in the suspension stirring method is tetrahydrofuran/water, 1,4-dioxane/toluene, acetonitrile/water, dimethyl sulfoxide/water, N,N-dimethylacetamide/water, ethyl acetate/n-heptane, chloroform/n-heptane, toluene/n-heptane, acetone/water, dichloromethane/n-heptane or N-methyl-2-pyrrolidinone/water.

In a third aspect, the present invention provides an anhydrous polymorph of a compound of formula I. The anhydrous polymorph of a compound of formula I has a crystalline form C. The XRPD pattern of the crystalline form C comprises peaks at the following 2θ angles: 5.2±0.2°, 10.4±0.2°, 13.4±0.25°, 15.0±0.2°, 16.4±0.2° and 29.1±0.2°.

Preferably, the XRPD pattern of the crystalline form C comprises peaks at the following 2θ angles: 5.2±0.2°, 10.4±0.2°, 13.4±0.2°, 15.0±0.2°, 16.4±0.2°, 19.6±0.2°, 20.1±0.2°, 22.8±0.2°, 24.4±0.2° and 29.1±0.2°.

More preferably, the XRPD pattern of the crystalline form C comprises peaks at the following 2θ angles: 5.2±0.2°, 10.4±0.2°, 11.9±0.2°, 13.4±0.2°, 15.0±0.2°, 16.4±0.2°, 17.3±0.2°, 19.6±0.2°, 20.1±0.2°, 22.8±0.2°, 23.6±0.2°, 24.4±0.2°, 29.1±0.2°, 31.6±0.2° and 34.1±0.2°.

Further preferably, the pattern of the crystalline form C is substantially consistent with FIG. 6.

Further, the TGA profile of the crystalline form C shows a weight loss of about 1.6% at 150±1° C.

Preferably, the TGA profile of the crystalline form C is substantially consistent with FIG. 7.

Further, the DSC profile of the crystalline form C shows heat absorption at 148±1° C., 167±1° C. and 177±1° C.

Preferably, the DSC profile of crystalline form C is substantially consistent with FIG. 7.

In a fourth aspect, the present invention provides a method for preparing an anhydrous polymorph with crystalline form C, which is selected from a slow volatilization method, a slow cooling method, a gas-solid diffusion method, a gas-liquid diffusion method, a polymer induction method, and an antisolvent addition method; preferably the antisolvent addition method.

Preferably, the solvent used in the slow volatilization method is at least one of a volatile alkyl alcohol, a volatile ketone, a volatile ether, a volatile aromatic hydrocarbon, a volatile ester, and a volatile chlorinated hydrocarbon; more preferably, the volatile alcohol is methanol, ethanol, or isopropanol; the volatile ketone is acetone, butanone, or methyl isobutyl ketone; and the volatile ether is ethyl ether, tetrahydrofuran, 2-methyltetrahydrofuran, 1,4-dioxane or methyl tert-butyl ether; the volatile aromatic hydrocarbon is toluene or xylene; the volatile ester is ethyl acetate or isopropyl acetate; and the volatile chlorinated hydrocarbon is dichloromethane, chloroform, or 1,2-dichloroethane; further preferably, the solvent mixture used in the slow volatilization method is ethanol/chloroform or tetrahydrofuran/isopropyl acetate.

Preferably, the solvent used in the slow cooling method is at least one of an alkyl alcohol, an alkyl ether, an alkyl ester, an aromatic hydrocarbon and an alkane; more preferably, the alkyl alcohol is methanol, ethanol or isopropanol; the alkyl ether is ethyl ether or methyl tert-butyl ether; the alkyl ester is ethyl acetate or isopropyl acetate; the aromatic hydrocarbon is toluene or xylene: and the alkane is n-pentane, n-hexane or n-heptane; further preferably, the solvent mixture used in the slow cooling method is toluene/isopropanol or isopropyl acetate/n-heptane. Also preferably, the lower limit temperature of the slow cooling method is 0-40° C.; the upper limit temperature is equal to or below the boiling point of the solvent, and the rate of cooling is 0.1-5° C./min. for example 0.1-2° C./min, 0.1-1° C./min, 0.1-0.5° C./min, 0.1-0.3° C./min or 0.1° C./min.

Preferably, the solvent used in the gas-solid diffusion method is a volatile ketone, a volatile ether or a volatile acid; more preferably, the volatile ketone is acetone or methyl isobutyl ketone: the volatile ether is ethyl ether, methyl tert-butyl ether, tetrahydrofuran, or 1,4-dioxane; and the volatile acid is acetic acid.

Preferably, the good solvent used in the gas-liquid diffusion method is an alkyl alcohol, an alkyl ketone, an alkyl ester, an alkyl ether, a chlorinated hydrocarbon, an aromatic hydrocarbon, or dimethyl sulfoxide; and the antisolvent is water, alkane, or alkyl alcohol; more preferably, for the good solvent, the alkyl alcohol is methanol, ethanol, or isopropanol; the alkyl ketone is acetone, butanone or methyl isobutyl ketone; the alkyl ester is ethyl acetate or isopropyl acetate, the alkyl ether is ether, methyl tert-butyl ether, 1,4-dioxane, tetrahydrofuran or 2-methyltetrahydrofuran: the chlorinated hydrocarbon is dichloromethane, chloroform or 1,2-dichloroethane; the aromatic hydrocarbon is toluene or xylene; and for the antisolvent, the alkane is n-heptane: and the alkyl alcohol is isopropanol. Further preferably, the good solvent/antisolvent combination used in the gas-liquid diffusion method is methanol/water, methyl isobutyl ketone/water, tetrahydrofuran/water, isopropyl acetate/n-heptane, 2-methyltetrahydrofuran/n-heptane, chloroform/n-heptane, toluene/n-heptane, ethanol/isopropyl alcohol, acetone/isopropyl alcohol, 1,4-dioxane/isopropanol or dimethyl sulfoxide/isopropanol.

Preferably, the good solvent used in the polymer induction method is an alkyl alcohol, an alkyl ketone, an alkyl ester, an alkyl ether, or a chlorinated hydrocarbon; preferably the alkyl alcohol is methanol, ethanol, or isopropanol; the alkyl ketone is acetone or methyl isobutyl ketone: the alkyl ester is ethyl acetate or isopropyl acetate; the alkyl ether is tetrahydrofuran, 2-methyltetrahydrofuran, or 1,4-dioxane, the chlorinated hydrocarbon is methylene chloride or 1,2-dichloroethane; the polymer used is any one or more of polyvinyl pyrrolidone, polyvinyl alcohol, polyvinyl chloride, polyvinyl acetate, hydroxypropyl methyl cellulose and methyl cellulose, preferably an equal mass mixture, or any one or more of polycaprolactone, polyethylene glycol, polymethyl methacrylate, sodium alginate and hydroxyethyl cellulose, preferably an equal mass mixture.

Preferably, the good solvent used in the antisolvent addition method is an alkyl alcohol, an alkyl ketone, an alkyl ester, a cyclic ether, a chlorinated hydrocarbon, an aromatic hydrocarbon, a chain or cyclic amide, or dimethyl sulfoxide; and the antisolvent used is an alkane or an ether; more preferably, for the good solvent, the alkyl alcohol is methanol, ethanol, or isopropanol; the alkyl ketone is methyl isobutyl ketone, acetone, or butanone; the alkyl ester is ethyl acetate or isopropyl acetate; the cyclic ether is 1,4-dioxane or 2-methyltetrahydrofuran; the chlorinated hydrocarbon is methylene chloride, chloroform or 1,2-dichloroethane; the aromatic hydrocarbon is benzene, toluene or xylene; the amide in chain form is N,N-dimethyl formamide or N,N-dimethyl acetamide; the amide in cyclic form is N-methyl-2-pyrrolidinone; and for the antisolvent, the alkane is n-pentane, n-hexane or n-heptane; and the ether is ethyl ether or methyl tert-butyl ether; further preferably, the good solvent/antisolvent combination used in the antisolvent addition method is methyl isobutyl ketone/n-heptane, ethyl acetate/n-heptane, 1,4-dioxane/n-heptane, dichloromethane/n-heptane, toluene/n-heptane, isopropyl acetate/methyl tert-butyl ether, N-methylpyrrolidone/methyl tert-butyl ether, 2-methyltetrahydrofuran/methyl tert-butyl ether or chloroform/methyl tert-butyl ether.

In a fifth aspect, the present invention provides an anhydrous polymorph of a compound of formula I. The anhydrous polymorph of a compound of formula I has a crystalline form B. The XRPD pattern of the crystalline form B comprises peaks at the following 2θ angles: 7.3±0.2°, 9.9±0.2°, 12.5±0.2°, 16.5±0.2° and 17.1±0.2°.

Preferably, the XRPD pattern of the crystalline form B comprises peaks at the following 2θ angles: 7.3±0.2°, 9.9±0.2°, 12.5±0.2°, 13.1±0.2°, 16.5±0.2°, 17.1±0.2°, 20.3±0.2°, 24.0±0.2°, 25.2±0.2° and 26.7±0.2°.

More preferably, the XRPD pattern of the crystalline form B comprises peaks at the following 2θ angles: 7.3±0.2°, 9.9±0.2°, 12.5±0.2°, 13.1±0.2°, 16.5±0.2°, 17.1±0.2°, 20.3±0.2°, 21.3±0.2°, 24.0±0.2°, 25.2±0.2°, 26.7±0.2°, 27.8±0.2°, 28.6±0.2°, 29.5±0.2° and 31.3±0.2°.

Further preferably, the pattern of the crystalline form B is substantially consistent with FIG. 8.

Further, the TGA profile of the crystalline form B shows a weight loss of about 1.5% at 150±1° C.

Preferably, the TGA profile of the crystalline form B is substantially consistent with FIG. 9.

Further, the DSC profile of the crystalline form B shows heat absorption at 177±1° C.

Preferably, The DSC profile of the crystalline form B is substantially consistent with FIG. 9.

In a sixth aspect, the present invention provides a method for preparing an anhydrous polymorph with crystalline form B, which is an antisolvent addition method.

Preferably, the good solvent used in the antisolvent addition method is an alkyl ketone, a chain or cyclic amide or dimethyl sulfoxide. Preferably, the alkyl ketone is methyl isobutyl ketone, acetone or butanone, the chain amide is N,N-dimethylformamide or N,N-dimethylacetamide, the cyclic amide is N-methyl-2-pyrrolidinone. The antisolvent used is water; more preferably, the combination of good solvent/antisolvent used in the antisolvent addition method is acetone/water, N,N-dimethylacetamide/water or dimethyl sulfoxide/water.

In a seventh aspect, the present invention provides an anhydrous polymorph of a compound of formula I. The anhydrous polymorph of a compound of formula I has a crystalline form A. The crystalline form A has an XRPD pattern comprises peaks at the following 2θ angles: 9.0±0.2°, 12.5±0.2°, 15.7±0.2°, 17.2±0.2°, 18.1±0.2° and 23.2±0.2°.

Preferably, the XRPD pattern of the crystalline form A comprises peaks at the following 2θ angles: 3.3±0.2°, 7.5±0.2°, 9.0±0.2°, 12.5±0.2°, 12.9±0.2°, 15.2±0.2°, 15.7±0.2°, 17.2±0.2°, 18.1±0.2°, 23.2±0.2°, 24.4±0.2°, 28.4±0.2° and 29.8±0.2°.

More preferably, the XRPD pattern of the crystalline form A comprises peaks at the following 2θ angles: 3.3±0.2°, 7.5±0.2°, 9.0±0.2°, 12.5±0.2°, 12.9±0.2°, 14.4±0.2°, 15.2±0.2°, 15.7±0.2°, 17.2±0.2°, 17.7±0.2°, 18.1±0.2°, 19.9±0.2°, 21.8±0.2°, 23.2±0.2°, 24.4±0.2°, 28.4±0.2° and 29.8±0.2°.

Further preferably, the pattern of the crystalline form A is substantially consistent with FIG. 10.

Further, the TGA profile of the crystalline form A shows a weight loss of about 1.0% at 150±1° C.

Preferably, the TGA profile of the crystalline form A is substantially consistent with FIG. 11.

Further, the DSC profile of the crystalline form A shows heat absorption at 160±1° C. and 177±1° C. and exothermic at 162±1° C.

Preferably, the DSC profile of the crystalline form A is substantially consistent with FIG. 11.

In an eighth aspect, the present invention provides a method for preparing an anhydrous polymorph with crystalline form A, which is an antisolvent addition method.

Preferably, the good solvent used in the antisolvent addition method is an alkyl alcohol, preferably methanol, ethanol or isopropanol; and the antisolvent used is water; more preferably, the good solvent/antisolvent combination used in the antisolvent addition method is methanol/water.

Preferably, the anhydrous polymorph of the compound of formula I of the present invention has a particle size of 5-100 microns.

More preferably, the particle size of the anhydrous polymorph of the compound of formula I of the present invention is 10-90 microns.

Further preferably, the particle size of the anhydrous polymorph of the compound of formula I of the present invention is 30-60 microns.

In a ninth aspect, the present invention provides a pharmaceutical composition comprising (preferably an effective amount for prevention, alleviation and/or treatment) an anhydrous polymorph of a compound of formula I, and a pharmaceutically acceptable excipient; preferably the anhydrous polymorph of the compound of formula I has a particle size of 5-100 microns (preferably 10-90 microns, more preferably 30-60 microns); preferably the pharmaceutical composition also comprises a second functional component; the second functional component is selected from any one or more of minoxidil, deuterated ruxolitinib (CTP-543), botulinum toxin, clascoterone (CB-03-01), finasteride and latanoprost.

Preferably, in the above-described pharmaceutical composition, the anhydrous polymorph of the compound of formula I has a weight percentage of 1.0%-99.0%, for example, the weight percentage can be 10.0%-80.0%、20%-80%、25%-80%、25%-70%、25%-65%、25%-60%、25%-55%、25%-50%、30%-50%、35%-50% or 40%-50%.

In a tenth aspect, the present invention provides use of an anhydrous polymorph or a pharmaceutical composition of the compound of formula I in the preparation of a medicament for the prevention, alleviation and/or treatment of a disease or condition associated with androgen receptor activity; preferably, the pharmaceutical composition further comprises a second functional component, and the second functional component is selected from any one or more of minoxidil, deuterated ruxolitinib, botulinum toxin, clascoterone, finasteride and latanoprost.

In an eleventh aspect, the present invention provides an anhydrous polymorph or a pharmaceutical composition of the compound of formula I for use in the prevention, alleviation and/or treatment of a disease or condition associated with androgen receptor activity; preferably, the pharmaceutical composition further comprises a second functional component, and the second functional component is selected from any one or more of minoxidil, deuterated ruxolitinib, botulinum toxin, clascoterone, finasteride and latanoprost.

In a twelfth aspect, the present invention provides a method for preventing alleviating and/or treating a disease or condition associated with androgen receptor activity, comprising the steps of administering the anhydrous polymorph or the pharmaceutical composition of a compound of formula I in a preventively, alleviatively and/or therapeutically effective amount to an individual in need thereof. Preferably, the pharmaceutical composition further comprises second functional component, and the second functional component is selected from any one or more of minoxidil, deuterated ruxolitinib, botulinum toxin, clascoterone, finasteride and latanoprost.

Preferably, in aspects from ten to twelve, the androgen receptor activity related disease or condition is selected from prostate cancer, benign prostatic hyperplasia, acne, hirsutism, excess sebum and male hair loss.

Effects of the Invention

The present invention provides four crystalline forms of the compound of formula I, all of which are anhydrous and have excellent thermal stability, and TGA weight loss % (for example, up to 150° C.) does not exceed 1.6%, and at the same time has a high melting point. At a high temperature (for example, above 166° C.), crystalline form B is the most stable crystalline form.

In the present invention, crystalline form D is more stable and has a low risk of crystal transformation under 5° C./room temperature (about 20° C.)/50° C./90° C.; the DVS result of the anhydrous polymorph of the compound of formula I in the form of crystalline form D shows that when the relative humidity increased from 0% RH to 80% RH at 25° C., the moisture absorption of the crystalline form D sample increased by only 0.14 wt %, indicating that the sample has almost no hygroscopicity. After being stored at 40° C./75% RH and 25° C./60% RH for one week, there were no significant changes in the crystalline form and chemical purity of the crystalline form D sample, indicating that the crystalline form D sample has good physical and chemical stability. All the crystalline forms A-D of the present invention are suitable as potential pharmaceutical crystalline forms, especially the crystalline forms B or D.

DETAILED DESCRIPTION OF THE INVENTION

Figure 1:
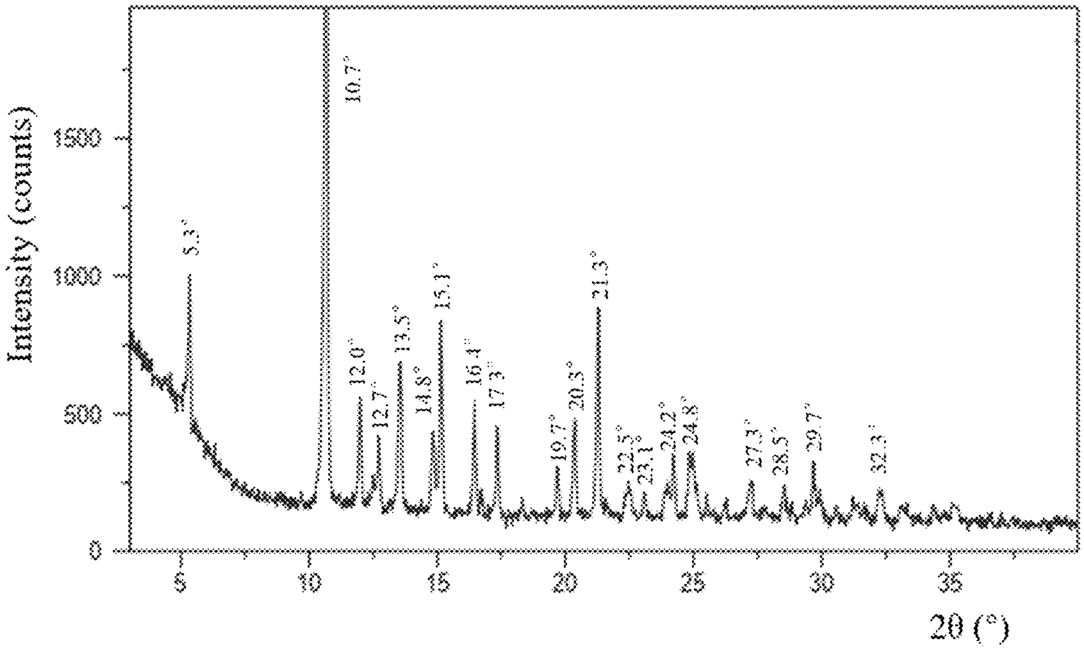
FIG. 1 shows an XRPD pattern of the anhydrous polymorph with crystalline form D of the compound of formula I.

Unless otherwise indicated, scientific and technical terms herein have the meanings commonly understood by those skilled in the art.

Unless otherwise indicated, words appearing herein in the singular form, such as “a”, “an”, and “the”, cover their corresponding plural referents unless the context clearly indicates the contrary. For example, when reference is made to “a” crystalline form or polymorph, one or more different crystalline forms or polymorphs are covered, and when reference is made to “the” method, equivalent steps and methods known to one of ordinary skill in the art are covered.

For crystalline forms herein, only the characteristic peaks (i.e., the most characteristic, significant, unique and/or reproducible diffraction peaks) in the XRPD pattern are summarized, whereas other peaks can be obtained from the patterns by conventional methods. The above characteristic peaks are repeatable within the limits of error (+0.2° error limit).

Unless otherwise indicated, the term "comprise" and variations thereof, such as "contain" and "include", appearing herein, indicates that the set covers not only one or more integers, steps or combinations thereof that are expressly disclosed, but also does not exclude any other integers, steps, or combinations thereof. Also, in certain circumstances, the term "comprise" as it appears herein may be replaced with the terms "contain", "include", or "have".

Unless otherwise indicated, the term "effective amount" as it appears herein denotes an amount of an active pharmaceutical ingredient that is sufficient to affect a disease or condition after the active pharmaceutical has ingredient been administered to an individual/subject/patient for the purpose of preventing, alleviating and/or treating the disease or condition. The "effective amount" may vary depending on the active pharmacological ingredient, the symptoms or severity of the disease or condition, the individual's/subject's/patient's personal situations (for example, age, gender, weight, etc.), and other factors.

Unless otherwise indicated, a pharmaceutical composition comprising the polymorph of the present invention may be administered by oral, inhalation, rectal, parenteral or topical routes to individuals/subjects/patients in need thereof. For oral administration, the pharmaceutical composition may be in a solid formulation (for example, tablets, powders, granules, capsules, etc.) or in a liquid formulation (for example, an aqueous or oil-based suspension or other liquid formulation, such as a syrup, solution, etc.). For parenteral administration, the pharmaceutical composition may be a solution, a suspension, a lyophilized powder etc. The pharmaceutical composition may be a single unit with a precise dosage. In addition, the pharmaceutical composition may further comprise additional active pharmaceutical ingredients.

Polymorphs of the Compound of Formula I

First, the present invention provides a first anhydrous polymorph of the compound of formula I with crystalline form D. The measured XRPD pattern is substantially consistent with FIG. 1.

It can be found from its XRPD pattern that the crystalline form D has diffraction peaks with higher relative intensity at the following 2θ angles: 5.3±0.2°, 10.7±0.2°, 13.5±0.2°, 15.1±0.2° and 21.3±0.2°.

In addition, crystalline form D has diffraction peaks of moderate relative intensity at the following 2θ angles: 12.0±0.2°, 12.7±0.2°, 14.8±0.2°, 16.4±0.2°, 17.3±0.2°, 20.3±0.2°, 24.2±0.2° and 24.8±0.2°.

In addition, crystalline form D also has diffraction peaks with lower relative intensity at the following 2θ angles: 19.7±0.2°, 22.5±0.2°, 23.1±0.2°, 27.3±0.2°, 28.5±0.2°, 29.7±0.2° and 32.3±0.2°.

In one example, the anhydrous polymorph of the compound of formula I of the present invention has a crystalline form D as described above, with a particle size of 5-100 microns, preferably 10-90 microns, more preferably 30-60 microns.

Secondly, the present invention provides a second anhydrous polymorph of the compound of formula I which has a crystalline form C. The measured XRPD pattern is substantially consistent with FIG. 6.

Through its XRPD pattern, it can be found that crystalline form C has diffraction peaks with higher relative intensity at the following 2θ angles: 5.2±0.2°, 10.4±0.2°, 13.4±0.2°, 15.0±0.2°, 16.4±0.2° and 29.1±0.2°.

In addition, crystalline form C also has diffraction peaks of moderate relative intensity at the following 2θ angles: 19.6±0.2°, 20.1±0.2°, 22.8±0.2° and 24.4±0.2°.

In addition, crystalline form C also has diffraction peaks of lower relative intensity at the following 2θ angles: 11.9±0.2°, 17.3±0.2°, 23.6±0.2°, 31.6±0.2° and 34.1±0.2°.

In one embodiment, the anhydrous polymorph of the compound of formula I of the present invention has a crystalline form C as described above with a particle size of 5-100 microns, preferably 10-90 microns, more preferably 30-60 microns.

Again, the present invention provides a third anhydrous polymorph of the compound of formula I which has crystalline form B. The measured XRPD pattern is substantially consistent with FIG. 8.

It can be found from its XRPD pattern that crystalline form B has diffraction peaks with higher relative intensity at the following 2θ angles: 7.3±0.2°, 9.9±0.2°, 12.5±0.2°, 16.5±0.2° and 17.1±0.2°.

In addition, crystalline form B also has diffraction peaks with moderate relative intensity at the following 2θ angles: 13.1±0.2°, 20.3±0.25°, 24.0±0.25°, 25.2±0.2°, and 26.7±0.2°.

In addition, crystalline form B also has diffraction peaks with lower relative intensity at the following 2θ angles: 21.3±0.2°, 27.8±0.2°, 28.6±0.2°, 29.5±0.2° and 31.3±0.2°.

In one embodiment, the anhydrous polymorph of the compound of formula I of the present invention has a crystalline form B as described above with a particle size of 5-100 microns, preferably 10-90 microns, more preferably 30-60 microns.

Finally, the present invention provides a fourth anhydrous polymorph of the compound of formula I which has crystalline form A. The measured XRPD pattern is substantially consistent with FIG. 10.

From its XRPD pattern, it can be found that crystalline form A has diffraction peaks with higher relative intensity at the following 2θ angles: 9.0±0.2°, 12.5±0.2°, 15.7±0.2°, 17.2±0.2°, 18.1±0.2° and 23.2=0.2°.

In addition, crystalline form A also has diffraction peaks of moderate relative intensity at the following 2θ angles: 3.3±0.2°, 7.5±0.2°, 12.9±0.2°, 15.2±0.2°, 24.4±0.2°, 28.4±0.2° and 29.8±0.2°.

In addition, crystalline form A has diffraction peaks of moderate relative intensity at the following 2θ angles: 14.4±0.2°, 17.7±0.2°, 19.9±0.2° and 21.8±0.2°.

In one embodiment, the anhydrous polymorph of the compound of formula I of the present invention has a crystalline form A as described above with a particle size of 5-100 microns, preferably 10-90 microns, more preferably 30-60 microns.

Preparation Method of Anhydrous Polymorphs

In the present invention, the anhydrous polymorph of the compound of formula I can be prepared by a slow volatilization method, a slow cooling method, a gas-solid diffusion method, a gas-liquid diffusion method, a polymer induction method, a grinding method, a suspension stirring method, or an antisolvent addition method.

When the anhydrous polymorph has crystalline form D, it can be prepared by a slow volatilization method, a gas-solid diffusion method, a gas-liquid diffusion method, a polymer induction method, a grinding method, or a suspension stirring method.

In one embodiment, the anhydrous polymorph with crystalline form D can be prepared by a slow volatilization method. The method comprises dissolving the compound of formula I in a solvent and performing slow volatilization at atmospheric pressure. The suitable solvent for the method may be, for example, a volatile halogenated alkane (for example, methylene chloride, chloroform etc.) or a straight-chain or branched C2-C6 nitrile (for example, acetonitrile, etc.).

In one embodiment, the anhydrous polymorph with crystalline form D can be prepared by a gas-solid diffusion method. The method comprises subjecting the compound of formula I in solid state to a gas phase atmosphere formed by volatilization of a solvent, so that the compound of formula I in solid state interacts with the solvent in gaseous state. The solvent suitable for the method may be, for example, a volatile alcohol (for example, methanol, ethanol, etc.) or a volatile ether (for example, ether, methyl tert-butyl ether, etc.).

In one embodiment, the anhydrous polymorph with crystalline form D can be prepared by a gas-liquid diffusion method. The method comprises dissolving the compound of formula I in a good solvent and then placing it in a gas phase atmosphere formed by volatilization of an antisolvent, so that the compound of formula I in the liquid state interacts with the antisolvent in the gaseous state. The good solvent suitable for the method may be, for example, a straight-chain or branched C2-C6 nitrile (for example, acetonitrile, etc.), while the antisolvent may be, for example, water. Suitable good solvent/antisolvent combinations may be, for example, acetonitrile/water.

In one embodiment, the anhydrous polymorph with crystalline form D can be prepared by a polymer induction method. The method comprises dissolving the compound of formula I in a good solvent and adding the polymer, followed by slow volatilization of the good solvent at atmospheric pressure. The good solvent suitable for the method may be, for example, a straight-chain or branched C2-C6 nitrile (for example, acetonitrile, etc.), and the polymers may be, for example, any one or more (for example, an equal-mass mixture) of polycaprolactone (PCL), polyethylene glycol (PEG), polymethyl methacrylate (PMMA), sodium alginate (SA), and hydroxyethyl cellulose (HEC).

In one embodiment, the anhydrous polymorph with crystalline form D can be prepared by a grinding method. The method comprises grinding the compound of formula I by placing it in a grinding device (for example, a mortar), optionally with the addition of a solvent. The solvent suitable for the method may be, for example, water.

In one embodiment, the anhydrous polymorph with crystalline form D can be prepared by a suspension stirring method (also known as beating method). The method comprises placing the compound of formula I with solid state in a solvent and stirring the formed suspension, preferably at 0-60° C., more preferably at 20-40° C. The solvent suitable for the method may be, for example, at least one of water, alkanes (for example, n-pentane, n-hexane, n-heptane, etc.), alkyl alcohols (for example, methanol, ethanol, isopropanol, etc.), alkyl ketones (for example, acetone, methyl isobutyl ketone, etc.), alkyl esters (for example, ethyl acetate, isopropyl acetate, etc.), chlorinated hydrocarbons (for example, dichloromethane, chloroform, etc.), ethers (for example, ethyl ether, methyl tert-butyl ether, 1,4-dioxane, 2-methyltetrahydrofuran, etc.), aromatic hydrocarbons (for example, benzene, toluene, xylene, etc.), straight-chain or branched C2-C6 nitriles (for example, acetonitrile, etc.), dimethyl sulfoxide, or an amide in a chain or cyclic form (for example, N,N-dimethylformamide, N,N-dimethylacetamide, N-methyl-2-pyrrolidone, etc.). When the method uses a mixed solvent formed from more than two solvents, the mixed solvent may be, for example, tetrahydrofuran/water (for example, volume ratio 1:2), 1,4-dioxane/toluene (for example, volume ratio 1:4), acetonitrile/water (for example, volume ratio 1:2), dimethyl sulfoxide/water (for example, volume ratio 1:1). N,N-dimethylacetamide/water (for example, volume ratio 1:1), ethyl acetate/n-heptane (for example, volume ratio 1:9), chloroform/n-heptane (for example, volume ratio 1:4), toluene/n-heptane (for example, volume ratio 1:4), acetone/water (for example, volume ratio 1:3), dichloromethane/n-heptane (for example, volume ratio 1:3), or N-methyl-2-pyrrolidone/water (for example, volume ratio 1:1).

When the anhydrous polymorph has crystalline form C, it can be prepared by a slow volatilization method, a slow cooling method, a gas-solid diffusion method, a gas-liquid diffusion method, a polymer induction method, or an anti-solvent addition method.

In one embodiment, the anhydrous polymorph which has crystalline form C can be prepared by a slow volatilization method. The solvent suitable for the method may be, for example, at least one of volatile alkyl alcohols (for example, methanol, ethanol, isopropanol, etc.), volatile ketones (for example, acetone, butanone, methyl isobutyl ketone, etc.), volatile ethers (for example, ethyl ether, tetrahydrofuran, 2-methyltetrahydrofuran, 1,4-dioxane, or methyl tert-butyl ether), volatile aromatic hydrocarbons (for example, toluene, xylene, etc.), volatile esters (for example, ethyl acetate, isopropyl acetate, etc.), volatile chlorinated hydrocarbons (for example, methylene chloride, chloroform, 1,2-dichloroethane, etc.). When the method uses a mixed solvent formed from more than two solvents, the mixed mixture may be, for example, ethanol/chloroform (for example, volume ratio 1:1) or tetrahydrofuran/isopropyl acetate (for example, volume ratio 1:1).

In one embodiment, the anhydrous polymorph with crystalline form C can be prepared by a slow cooling method. The method comprises dissolving the compound of formula I in a solvent which has a temperature below the boiling point and then slowly cooling (for example, 0.1° C./min) to 0-40° C. The solvent suitable for the method may be, for example, at least one of alkyl alcohols (for example, methanol, ethanol, isopropanol, etc.), alkyl ethers (for example, ethyl ether, methyl tert-butyl ether, etc.), alkyl esters (for example, ethyl acetate, isopropyl acetate, etc.), aromatic hydrocarbons (for example, toluene, xylene, etc.), and alkane hydrocarbons (for example, n-pentane, n-hexane, n-heptane, etc.). When the method uses a mixed solvent formed from more than two solvents, the mixed solvent may be, for example, toluene/isopropanol (for example, volume ratio 1/9) or isopropyl acetate/n-heptane (for example, volume ratio 1/4).

In one embodiment, the anhydrous polymorph with crystalline form C can be prepared by a gas-solid diffusion method. The solvent suitable for the method may be, for example, a volatile ketone (for example, acetone, methyl isobutyl ketone, etc.), a volatile ether (for example, ethyl ether, methyl tert-butyl ether, tetrahydrofuran, 1,4-dioxane, etc.), or a volatile acid (for example, acetic acid).

In one embodiment, the anhydrous polymorph with crystalline form C can be prepared by a gas-liquid diffusion method. A good solvent suitable for the method may be, for example, an alkyl alcohol (for example, methanol, ethanol isopropanol, etc.), an alkyl ketone (for example, acetone, butanone, methyl isobutyl ketone, etc.), an alkyl ester (for example, ethyl acetate, isopropyl acetate, etc.), an alkyl ether (for example, ethyl ether, methyl tert-butyl ether, 1,4-dioxane, tetrahydrofuran, 2-methyltetrahydrofuran, etc.), a chlorinated hydrocarbon (for example, dichloromethane, chloroform, 1,2-dichloroethane, etc.), an aromatic hydrocarbon (for example, toluene, xylene, etc.), or dimethyl sulfoxide; whereas the antisolvent may be, for example, water, an alkane (for example, n-heptane, etc.), or an alkyl alcohol (for example, isopropanol, etc.). A suitable good solvent/antisolvent combination can be, for example, methanol/water, methyl isobutyl ketone/water, tetrahydrofuran/water, isopropyl acetate/n-heptane, 2-methyltetrahydrofuran/n-heptane, chloroform/n-heptane, toluene/n-heptane, ethanol/isopropyl alcohol, acetone/isopropyl alcohol, 1,4-dioxane/isopropanol, or dimethyl sulfoxide/isopropyl alcohol.

In one embodiment, the anhydrous polymorph with crystalline form C can be prepared by a polymer induction method. A good solvent suitable for the method may be, for example, an alkyl alcohol (for example, methanol, ethanol, isopropanol, etc.), an alkyl ketone (for example, acetone, methyl isobutyl ketone, etc.), an alkyl ester (for example, ethyl acetate, isopropyl acetate, etc.), an alkyl ether (for example, tetrahydrofuran, 2-methyltetrahydrofuran, 1,4-dioxane, etc.) or a chlorinated hydrocarbon (for example, dichloromethane, 1,2-dichloroethane, etc.); and the polymer may be, for example, any one of polyvinyl pyrrolidone (PVP), polyvinyl alcohol (PVA), polyvinyl chloride (PVC), polyvinyl acetate (PVAc), hydroxypropyl methyl cellulose (HPMC), and methyl cellulose (MC), or a mixture thereof (for example, an equal mass mixture), or any one of polycaprolactone (PCL), polyethylene glycol (PEG), poly methyl methacrylate (PMMA), sodium alginate (SA) and hydroxyethyl cellulose (HEC), or a mixture thereof (for example, an equal mass mixture).

In one embodiment, the anhydrous polymorph with crystalline form C can be prepared by an antisolvent addition method. The method comprises dissolving the compound of formula I in a good solvent and then adding an antisolvent. Wherein the solubility of the compound of formula I in the good solvent is greater than the solubility in the antisolvent, and the addition of the antisolvent to the good solvent can make the compound of formula I dissolved in the good solvent precipitate solid. The good solvent suitable for the method may be, for example, an alkyl alcohol (for example, methanol, ethanol, isopropanol, etc.), an alkyl ketone (for example, methyl isobutyl ketone, acetone, butanone, etc.), an alkyl ester (for example, ethyl acetate, isopropyl acetate, etc.), a cyclic ether (for example, 1,4-dioxane, 2-methyltetrahydrofuran, etc.), a chlorinated hydrocarbon (for example, dichloromethane, chloroform, 1,2-dichloroethane, etc.), an aromatic hydrocarbon (for example, benzene, toluene, xylene, etc.), a chain or cyclic amide (for example, N,N-dimethylformamide, N,N-dimethylacetamide, N-methyl-2-pyrrolidone, etc.), or dimethyl sulfoxide: whereas the antisolvent may be, for example, an alkane (for example, n-pentane, n-hexane, n-heptane, etc.) or an ether (for example, ethyl ether, methyl tert-butyl ether, etc.). A suitable good solvent/antisolvent combination can be, for example, methyl isobutyl ketone/n-heptane, ethyl acetate/n-heptane, 1,4-dioxane/n-heptane, dichloromethane/n-heptane, toluene/n-heptane, isopropyl acetate/methyl tert-butyl ether, N-methyl-2-pyrrolidone/methyl tert-butyl ether, 2-methyltetrahydrofuran/methyl tert-butyl ether, or chloroform/methyl tert-butyl ether.

When the anhydrous polymorph has crystalline form B or crystalline form A, it can be prepared by an antisolvent addition method.

In one embodiment, the anhydrous polymorph with crystalline form B can be prepared by an antisolvent addition method. A good solvent suitable for the method may be, for example, an alkyl ketone (for example, methyl isobutyl ketone, acetone, butanone, etc.), a chain or cyclic amide (for example, N,N-dimethylformamide, N,N-dimethylacetamide, N-methylpyrrolidone, etc.), or dimethyl sulfoxide; whereas the antisolvent may be, for example, an alkane (for example, n-pentane, n-hexane, n-heptane, etc.) or water. A suitable good solvent/antisolvent combination can be, for example, acetone/water, N,N-dimethylacetamide/water, or dimethyl sulfoxide/water.

In one embodiment, the anhydrous polymorph with crystalline form A can be prepared by an antisolvent addition method. A suitable good solvent for the method may be, for example, an alkyl alcohol (for example, methanol, ethanol, isopropanol, etc.); and an antisolvent may be, for example, water. A suitable good solvent/antisolvent combination may be, for example, methanol/water.

Pharmaceutical Compositions

The present invention provides a pharmaceutical composition comprising (preferably an effective amount for prevention, alleviation and/or treatment) an anhydrous polymorph of a compound of formula I, and a pharmaceutically acceptable excipient.

In one embodiment, the pharmaceutical composition comprises (1) an anhydrous polymorph of the compound of formula I in an effective amount for prevention, alleviation and/or treatment, and (2) at least one pharmaceutically acceptable excipient.

In one embodiment, the anhydrous polymorph of the compound of formula I is 1.0%-99.0% by weight of the pharmaceutical composition.

In one embodiment, the anhydrous polymorph of the compound of formula I in the pharmaceutical composition (for example, which has crystalline form A, B, C, and/or D) has a particle size of 5-100 microns, preferably 10-90 microns, more preferably 30-60 microns.

The present invention also provides a pharmaceutical composition comprising (preferably an effective amount for prevention, alleviation and/or treatment) an anhydrous polymorph of the compound of formula I, (preferably an effective amount for prevention, alleviation and/or treatment) a second functional component, and a pharmaceutically acceptable excipient.

In one embodiment, the pharmaceutical composition comprises (1) an anhydrous polymorph of the compound of formula I in an effective amount for prevention, alleviation and/or treatment, (2) a second functional component in an effective amount for prevention, alleviation and/or treatment, and (3) at least one pharmaceutically acceptable excipient.

In one embodiment, the second functional component in the pharmaceutical composition is selected from any one or more of minoxidil, deuterated ruxolitinib, botulinum toxin, clascoterone, finasteride and latanoprost, and the anhydrous polymorph of the compound of formula I has a weight percentage and/or particle size as described above.

In one embodiment, the pharmaceutical compositions of the invention are tablets (preferably coated tablets), capsules, suppositories, nasal sprays or injections, preferably tablets or capsules.

Medical Use

The compound of formula I used as androgen receptor antagonist is capable of effectively responding to diseases or conditions associated with androgen receptor activity, and therefore the anhydrous polymorph or its pharmaceutical composition of the compound of formula I can likewise be used as androgen receptor antagonist, and thus be used for the prevention, alleviation and/or treatment of diseases or conditions associated with androgen receptor activity.

At the same time, the present invention provides the use of anhydrous polymorph or its pharmaceutical composition of the compound of formula I in the preparation of a medicament for the prevention, alleviation and/or treatment of a disease or condition associated with androgen receptor activity.

Additionally, the present invention provides a method for preventing, alleviating and/or treating a disease or condition associated with androgen receptor activity, comprising the steps of administering the anhydrous polymorph or the pharmaceutical composition of a compound of formula I in a preventively, alleviatively and/or therapeutically effective amount to a subject in need thereof.

In one embodiment, the disease or condition associated with androgen receptor activity is selected from prostate cancer, benign prostatic hyperplasia, acne, hirsutism, excess sebum and androgenetic alopecia.

The invention will be further elaborated below by specific examples. Unless otherwise indicated, the instruments, reagents and material, etc., used in the following examples are available by conventional commercial means.

Sources of the Compound of Formula I in Examples of the Present Invention

The title compound in essentially colloidal or viscous state was prepared as disclosed in paragraphs to on page 50 of the specification of CN 102757389 B. The title compound was dissolved by DMSO, and precipitated as a solid by dropwise addition of water, and filtered to collect the filter cake, and dried under reduced pressure at 40-50° C. The compound of formula I was obtained in solid state.

X-Ray Powder Diffraction (XRPD)

The XRPD pattern was acquired on a PANalytacal Empyrean X-ray powder diffraction analyzer and the test parameters were shown in Table 1.

TABLE 1

XRPD parameters

| Parameters | XRPD (Reflection Mode) |
|---|---|
| X ray | Cu, kα, kα1(Å): 1.540598; kα2 (Å): 1.544426 kα2/kα1 intensity ratio: 0.50 |
| Setting of X-ray light tube | 45 kV, 40 mA |
| Divergent slit | Automatic |
| Monochromator | none |
| Mode of scanning | Continuous |
| Scan range (°, 2θ) | 3-40 |
| Scan step (°, 2θ) | 0.0263/0.0167 |
| Scan frequency (°/min) | about 7 |

Thermogravimetric Analysis (TGA) and Differential Scanning Calorimetry (DSC)

TGA and DSC profiles were collected respectively on a TA Q500/5000 thermal gravimetric analyzer and a TA Q200/2000 differential scanning calorimeter, and the test parameters were shown in Table 2.

TABLE 2

TGA and DSC parameters

| Parameters | TGA | DSC |
|---|---|---|
| Method | Linear heating up | Linear heating up |
| Sample plate | Platinum plate, open | Aluminum pan, cover |
| Temperature range | Room Temperature-Set the end point temperature | 25° C.-Set the end point temperature |
| Scan rate (° C./min) | 10 | 10 |
| Protective gas | Nitrogen | Nitrogen |

Dynamic Vapor Sorption (DVS)

The DVS curves were collected on a DVS Intrinsic Dynamic Moisture Sorption meter from SMS (Surface Measurement Systems). The relative humidity at 25° C. was corrected with the deliquescence points of LiCl, Mg $(NO_3)_2$ and KCl. The DVS test parameters were shown in Table 3.

TABLE 3

DVS Parameters

| Parameters | Set value |
|---|---|
| temperature | 25° C. |
| Sample amount | 10-20 mg |
| Protective gas and flow rate | Nitrogen, 200 mL/min |
| dm/dt | 0.002%/min |
| Minimum dm/dt balance time | 10 min |
| Maximum dm/dt balance time | 180 min |
| RH range | 0% RH-90% RH-0% RH |
| RH gradient | 10% (0% RH-90% RH, 90% RH-0% RH) 5% (90% RH-95% RH, 95% RH-90% RH) |

High Performance Liquid Chromatography (HPLC)

The HPLC results were collected on an Agilent HPLC analyzer, and test parameters were shown in Table 4.

TABLE 4

HPLC Parameters

| Parameters | Parameter values/set values | |
|---|---|---|
| Instrument | Agilent 1260, DAD detector | |
| Chromatographic column | 42# Waters C1, 150 × 4.6 mm, 5 μm | |
| Mobile phase | A: 0.1% formic acid aqueous solution, B: acetonitrile | |
| | Time (minutes) | B % |
| Gradient | 0.0 | 10 |
| | 18.0 | 90 |
| | 20.0 | 90 |
| | 20.1 | 10 |
| | 24.0 | 10 |
| Run time | 24.0 min | |
| Post run time | 4.0 min | |
| flow rate | 1.0 mL/min | |
| Injection volume | 5 μL | |
| Wavelength of detection | UV detection wavelength was 268 nm, reference limit 400 nm | |

TABLE 4-continued

| HPLC Parameters | |
|---|---|
| Column temperature | 40° C. |
| Automatic injection temperature | Room temperature |
| Diluted solvent | Acetonitrile |

Example 1: Preparation of Anhydrous Polymorphs with Crystalline Form D

Method 1: Suspension Stirring Method

Specific operation: different solvents were used to set up different suspension stirring experiments. About 150 mg of compound of formula I was taken in a 15 mL reaction flask, 5 mL of solvent was added, and the formulated suspension was stirred at room temperature (20° C.) for 2 days, then the solid was collected and subjected to XRPD test.

The results showed that anhydrous polymorph with crystalline form D can be obtained at room temperature (about 20° C.) in the presence of water, methanol, ethanol, isopropanol, methyl isobutyl ketone, isopropyl acetate, methyl tert-butyl ether, 2-methyltetrahydrofuran, tetrahydrofuran/water ($V_{THF}/V_{H2O}$=1:2), 1,4-dioxane/toluene ($V_{diox}/V_{tol}$=1/4), acetonitrile/water ($V_{ACN}/V_{H2O}$=1/2), dimethyl sulfoxide/water ($V_{DMSO}/V_{H2O}$=1/1), N,N-dimethylacetamide/water ($V_{DMAc}/V_{H2O}$=1/1), ethyl acetate/n-heptane ($V_{EtOAc}/V_{n\text{-}hept}$=1/9), chloroform/n-heptane ($V_{TCM}/V_{n\text{-}hept}$=1/4) or toluene/n-heptane ($V_{tol}/V_{n\text{-}hept}$=1/4) as solvent.

The present invention further verified the product obtained by suspension stirring method at environment temperatures of 5° C. and 50° ° C.

The results showed that anhydrous polymorph with crystalline form D could be obtained at 5° C. in the presence of ethanol, methyl isobutyl ketone, ethyl acetate, 2-methyltetrahydrofuran, toluene, or dichloromethane/n-heptane ($V_{DCM}/V_{n\text{-}hept}$=1/3) as solvent; and anhydrous polymorph with crystalline form D could be obtained at 50° C. in the presence of isopropanol, acetone/water ($V_{ACTN}/V_{H2O}$=1/3), isopropyl acetate, methyl tert-butyl ether, or N-methyl-2-pyrrolidone/water ($V_{NMP}/V_{H2O}$=1/1) as solvent.

The XRPD pattern and detailed data of the anhydrous polymorph with crystalline form D are shown in FIG. 1 and Table 5.

TABLE 5

XRPD pattern data corresponding to crystalline form D

| No. | 2θ (°) | Relative intensity (%) |
|---|---|---|
| 1 | 5.3 | 11.7 |
| 2 | 10.7 | 100.0 |
| 3 | 12.0 | 8.8 |
| 4 | 12.7 | 5.7 |
| 5 | 13.5 | 12.2 |
| 6 | 14.8 | 6.1 |
| 7 | 15.1 | 15.1 |
| 8 | 16.4 | 9.7 |
| 9 | 17.3 | 7.0 |
| 10 | 18.3 | 1.3 |
| 11 | 19.7 | 4.1 |
| 12 | 20.3 | 7.7 |
| 13 | 21.3 | 16.9 |
| 14 | 22.5 | 2.7 |
| 15 | 23.1 | 2.0 |
| 16 | 24.2 | 5.1 |
| 17 | 24.8 | 5.4 |
| 18 | 26.2 | 1.2 |

TABLE 5-continued

XRPD pattern data corresponding to crystalline form D

| No. | 2θ (°) | Relative intensity (%) |
|---|---|---|
| 19 | 27.3 | 2.9 |
| 20 | 28.5 | 2.2 |
| 21 | 29.7 | 4.5 |
| 22 | 31.3 | 1.3 |
| 23 | 32.3 | 2.4 |
| 24 | 33.2 | 1.0 |
| 25 | 34.4 | 1.1 |
| 26 | 35.1 | 1.4 |

Figure 2:
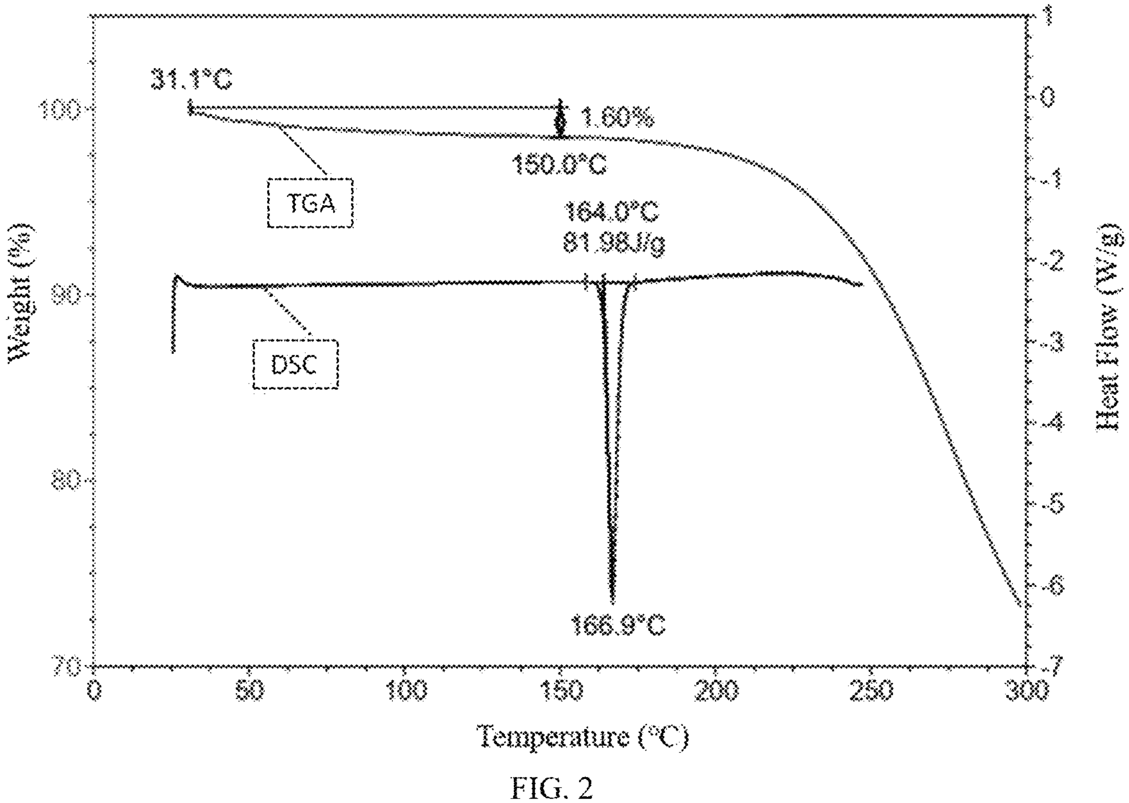
FIG. 2 shows a TGA/DSC profile of the anhydrous polymorph with crystalline form D of the compound of formula I.

The TGA/DSC profile of the anhydrous polymorph with crystalline form D is shown in FIG. 2. FIG. 2 shows that when heated to about 150° C., the weight loss of the sample is about 1.60%, and there is a sharp melting endothermic peak at about 164.0° C. (starting temperature) (melting point about 166.9° C.). According to the above data, the polymorph with the form D is an anhydrous polymorph.

Method 2: Slow Volatilization Method

Specific operation: Different solvents were used to set up different slow volatilization experiments. About 1 g of compound of formula I was taken and put into a reaction flask, and then added with 50 mL of solvent. After stirring and filtering, the liquid supernatant was taken and put into a vial, and sealed with a sealing film (for example, Parafilm), and then 3-4 small holes were punctured on the sealing film (for example, using a syringe needle). The small bottle was put at room temperature for slow volatilization, and after the solvent was completely dried up, the solid was collected and subjected to XRPD test.

It was identified that anhydrous polymorph with crystalline form D was obtained under condition of acetonitrile or dichloromethane as solvent.

Method 3: Gas-Solid Diffusion Method

Specific operation: Different solvents were used to set up different gas-solid diffusion experiments. About 10 mg of compound of formula I was taken in a 3 mL vial. About 2 mL of solvent was added in a 20 mL vial. The 3 mL vial was placed open in the 20 mL vial and then the 20 mL vial was sealed. After standing at room temperature for 7 days, the solid was collected and subjected to XRPD test.

It was identified that anhydrous polymorph with crystalline form D was obtained under either methanol or methyl tert-butyl ether as solvent.

Method 4: Gas-Liquid Diffusion Method

Specific operation: About 10 mg of compound of formula I was taken and dissolved in 1.0-2.0 mL of acetonitrile (as a good solvent), and filtered to obtain the liquid supernatant. The liquid supernatant was transferred to a 3.0 mL vial. Another 20 mL vial was taken, and added with about 3 mL of water (as an antisolvent). The 3 mL vial with the liquid supernatant was placed open in the 20 mL vial, and then the 20 ml vial was sealed and allowed to stand at room temperature. When solid precipitation was observed, the solid was separated and subjected to XRPD test.

After identification, the anhydrous polymorph with crystalline form D was identified.

Method 5: Polymer Induction Method

Specific operation: about 10 mg of compound of formula I was weighed and dissolved in acetonitrile (as a good solvent) in a vial, and then added with about 2 mg of polymers (equal mass mixture of polycaprolactone, polyethylene glycol, polymethyl methacrylate, sodium alginate, and hydroxyethyl cellulose). The vial was sealed by using a sealing film, and 3-4 holes were punched on the sealing film, and placed to be volatilized in room temperature condition to collect solid. And then the solid was subjected to XRPD Test.

After identification, the anhydrous polymorph with crystalline form D was identified.

Method 6: Grinding Method

Specific operation: about 15-20 mg of compound of formula I was weighed, and added to the mortar, and about 100 μL of water was dropwise added as solvent or no solvent was added. After grinding manually for 5-10 min, ground solid was collected and subjected to XRPD test.

After identification, the anhydrous polymorph with crystalline form D was obtained.

Example 2: Preparation of Anhydrous Polymorph with Crystalline Form C

Method 1: Antisolvent Addition Method

Specific operation: Different combinations of good solvent/antisolvent were used to set up different antisolvent addition experiments. About 10 mg of compound of formula I was taken and put in a 20.0 mL vial, dissolved with 0.2-1.0 mL of good solvent, and dropwise added with the antisolvent to the clear solution while stirring. The dropwise addition was stopped when there was solid precipitation, and the precipitated solid was separated by centrifugation and subjected to XRPD test.

The results showed that anhydrous polymorph with crystalline form C can be obtained under the conditions of good solvent/antisolvent combinations of methyl isobutyl ketone/n-heptane, ethyl acetate/n-heptane, 1,4-dioxane/n-heptane, dichloromethane/n-heptane, toluene/n-heptane, isopropyl acetate/methyl tert-butyl ether, N-methyl-2-pyrrolidinone/methyl tert-butyl ether, 2-methyltetrahydrofuran/methyl tert-butyl ether or chloroform/methyl tert-butyl.

Figure 6:
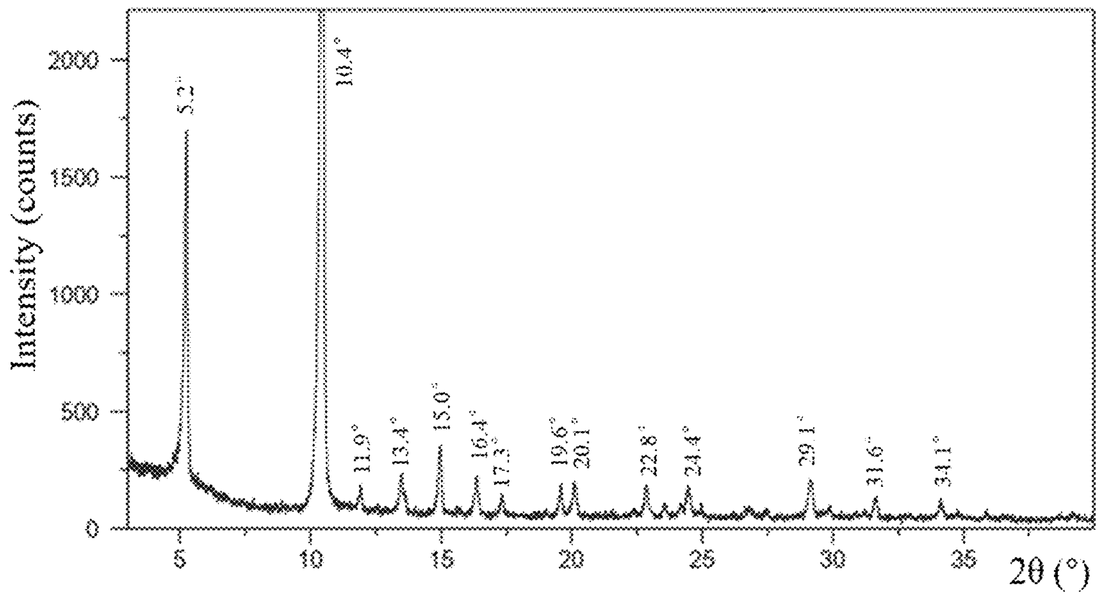
FIG. 6 shows an XRPD pattern of the anhydrous polymorph with crystalline form C of the compound of formula I.

The XRPD pattern and detailed data of the anhydrous polymorph with crystalline form C are shown in FIG. 6 and Table 6.

TABLE 6

XRPD pattern data corresponding to crystalline form C.

| No. | 2θ (°) | Relative intensity (%) |
|---|---|---|
| 1 | 5.2 | 26.7 |
| 2 | 10.4 | 100.0 |
| 3 | 11.9 | 1.8 |
| 4 | 13.4 | 3.0 |
| 5 | 15.0 | 4.9 |
| 6 | 16.4 | 3.0 |
| 7 | 17.3 | 1.4 |
| 8 | 19.6 | 2.2 |
| 9 | 20.1 | 2.3 |
| 10 | 22.8 | 2.4 |
| 11 | 23.6 | 1.0 |
| 12 | 24.4 | 2.2 |
| 13 | 26.7 | 0.6 |
| 14 | 27.4 | 0.5 |

TABLE 6-continued

XRPD pattern data corresponding to crystalline form C.

| No. | 2θ (°) | Relative intensity (%) |
|---|---|---|
| 15 | 29.1 | 3.0 |
| 16 | 29.9 | 0.7 |
| 17 | 31.6 | 1.4 |
| 18 | 34.1 | 1.2 |

Figure 7:
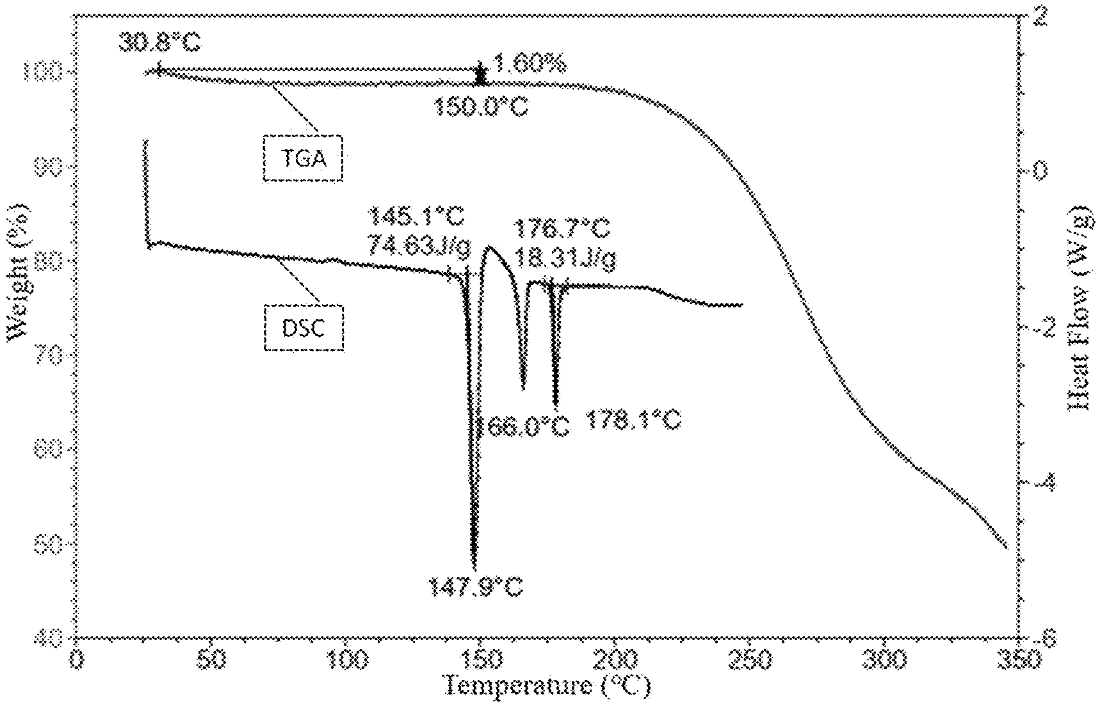
FIG. 7 shows a TGA/DSC profile of the anhydrous polymorph with crystalline form C of the compound of formula I.

The TGA/DSC profile of the anhydrous polymorph with crystalline form C is shown in FIG. 7. FIG. 7 shows that when heated to about 150.0° C., the weight loss of the sample is about 1.60%, and there are multiple endothermic/exothermic signal peaks before heating and decomposition. According to the above data, the polymorph with the form C is an anhydrous polymorph.

Method 2: Slow Volatilization Method

Operation was performed according to the corresponding method of crystalline form D.

It was identified that anhydrous polymorph with crystalline form C can be obtained under the condition of solvent of methanol, acetone, ethyl acetate, 1,4-dioxane, 2-methyltetrahydrofuran, toluene, ethanol/chloroform ($V_{EtOH}/V_{TCM}$=1:1) or tetrahydrofuran/isopropyl acetate ($V_{THF}/V_{IPAc}$=1:1).

Method 3: Slow Cooling Method

Specific operation: Different solvents were used to set up different slow cooling experiments. About 15 mg of compound of formula I was taken in a 3 mL vial, 1.0 mL of solvent was added, and filtered after stirring at 50° C. for about 2 h. The liquid supernatant was taken and placed in a biological incubator that was slowly cooled down (for example, at a rate of 0.1° C./min) from 50° C. to 5° C. and kept at a constant temperature of 5° C., and the precipitated solid was collected and subjected to XRPD test.

It was identified that anhydrous polymorph with crystalline form C was obtained under the conditions of solvents of ethanol, methyl tert-butyl ether, toluene/isopropanol ($V_{tol}/V_{IPA}$=1/9) or isopropyl acetate/n-heptane ($V_{IPAc}/V_{n\text{-}hept}$=1/4).

Method 4: Gas-Solid Diffusion Method

Operation was performed according to the corresponding method of crystalline form D.

It was identified that anhydrous polymorph with crystalline form C could be obtained under the condition of solvent of acetone, tetrahydrofuran, 1,4-dioxane or acetic.

Method 5: Gas-Liquid Diffusion Method

Operation was performed according to the corresponding method of crystalline form D.

It was identified that anhydrous polymorphs with crystalline form C could be obtained under the conditions of good solvent/antisolvent combinations of methanol/water, methyl isobutyl ketone/water, tetrahydrofuran/water, isopropyl acetate/n-heptane, 2-methyltetrahydrofuran/n-heptane, chloroform/n-heptane, toluene/n-heptane, ethanol/isopropyl alcohol, acetone/isopropyl alcohol, 1,4-dioxane/isopropanol or dimethyl sulfoxide/isopropanol.

Method 6: Polymer Induction Method

Operation was performed according to the corresponding method of crystalline form D.

It was identified that anhydrous polymorph with crystalline form C could be obtained under the condition of using equal mass mixtures of polyvinyl pyrrolidone, polyvinyl alcohol, polyvinyl chloride, polyvinyl acetate, hydroxypropyl methyl cellulose, and methyl cellulose as polymers, and using methanol, acetone, ethyl acetate, 1,4-dioxane, or dichloromethane as good solvents. In addition, anhydrous polymorph with crystalline form C can also be obtained under the condition of using equal mass mixtures of polycaprolactone, polyethylene glycol, polymethyl methacrylate, sodium alginate, and hydroxyethyl cellulose as polymers, and using ethanol, methyl isobutyl ketone, isopropyl acetate, or 2-methyltetrahydrofuran as good solvents.

Example 3: Preparation of Anhydrous Polymorphs with Crystalline Form B

Method 1: Antisolvent Addition Method

Operation was performed according to the corresponding method of crystalline form C.

It was identified that anhydrous polymorph with crystalline form B could be obtained under the conditions of good solvent/antisolvent combinations of acetone/water, N,N-dimethylacetamide/water, or dimethyl sulfoxide/water.

Figure 8:
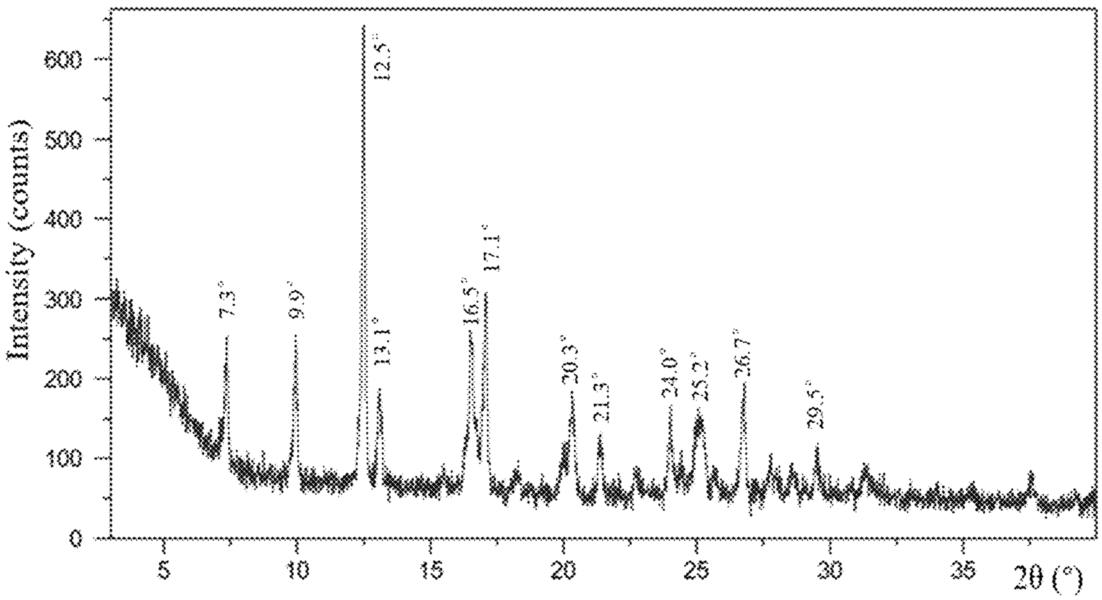
FIG. 8 shows an XRPD pattern of the anhydrous polymorph with crystalline form B of the compound of formula I.

The XRPD pattern and detailed data of the anhydrous polymorph with crystalline form B are shown in FIG. 8 and Table 7.

TABLE 7

XRPD pattern data corresponding to crystalline form B.

| No. | 2θ (°) | Relative intensity (%) |
|---|---|---|
| 1 | 7.3 | 24.9 |
| 2 | 9.9 | 31.9 |
| 3 | 12.5 | 100.0 |
| 4 | 13.1 | 19.9 |
| 5 | 16.5 | 35.0 |
| 6 | 17.1 | 41.0 |
| 7 | 18.2 | 4.0 |
| 8 | 20.3 | 18.8 |
| 9 | 21.3 | 11.1 |
| 10 | 22.7 | 4.8 |
| 11 | 24.0 | 15.6 |
| 12 | 25.2 | 14.6 |
| 13 | 26.7 | 21.1 |
| 14 | 27.8 | 6.1 |
| 15 | 28.6 | 6.2 |
| 16 | 29.5 | 8.4 |
| 17 | 31.3 | 6.0 |
| 18 | 37.5 | 4.8 |

Figure 9:
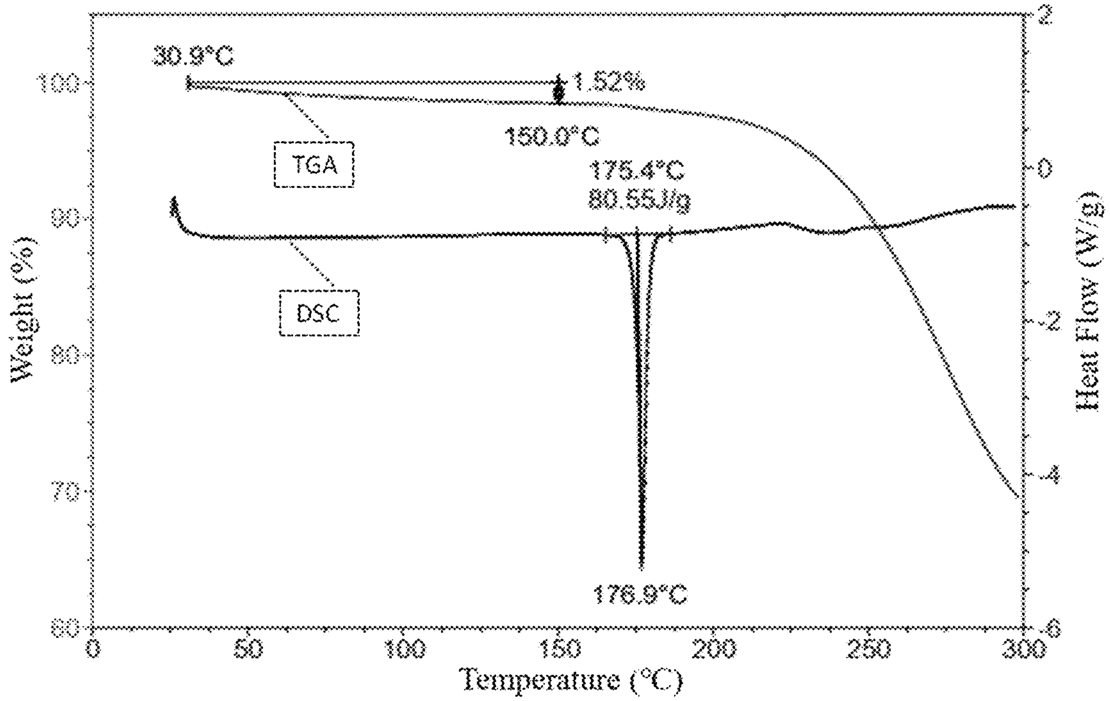
FIG. 9 shows a TGA/DSC profile of the anhydrous polymorph with crystalline form B of the compound of formula I.

The TGA/DSC profile of the anhydrous polymorph with crystalline form B is shown in FIG. 9. FIG. 9 shows that when heated to about 150.0° C., the weight loss of the sample is about 1.52%, and there is a sharp melting absorption peak at about 175.4° C. (starting temperature) (melting point about 176.9° C.). According to the above data the polymorph with form B is an anhydrous polymorph.

It was worth noting that various screening methods for solid phase transition and solution crystallization were performed, including the antisolvent addition method (a combination of methanol, acetone, tetrahydrofuran, acetonitrile, N,N-dimethylacetamide or dimethyl sulfoxide (good solvent) and water (antisolvent); a combination of methyl isobutyl ketone, ethyl acetate, 1, 4-dioxane, dichloromethane or toluene (good solvent) and n-heptane (antisolvent); a combination of isopropyl acetate, N-methyl-2-pyrrolidone, 2-methyltetrahydrofuran or chloroform (good solvent) and methyl tert-butyl ether (antisolvent)), slow volatilization method, slow cooling method, suspension stirring method (5° C./room temperature/50° C.), gas-solid infiltration method, gas-liquid infiltration method, polymer induction method and grinding method. It was found that the anhydrous polymorph with form B could be formed only by the antisolvent addition method and under the conditions of acetone/water, N,N-dimethylacetamide/water or dimethyl sulfoxide/water as a good solvent/antisolvent combination.

Example 4: Preparation of Anhydrous Polymorphs with Crystalline Form A

Operation was performed according to the corresponding method of crystalline form C or B.

It was identified that an anhydrous polymorph with crystalline form A could be obtained under the condition of methanol/water as a good solvent/antisolvent combination.

Figure 10:
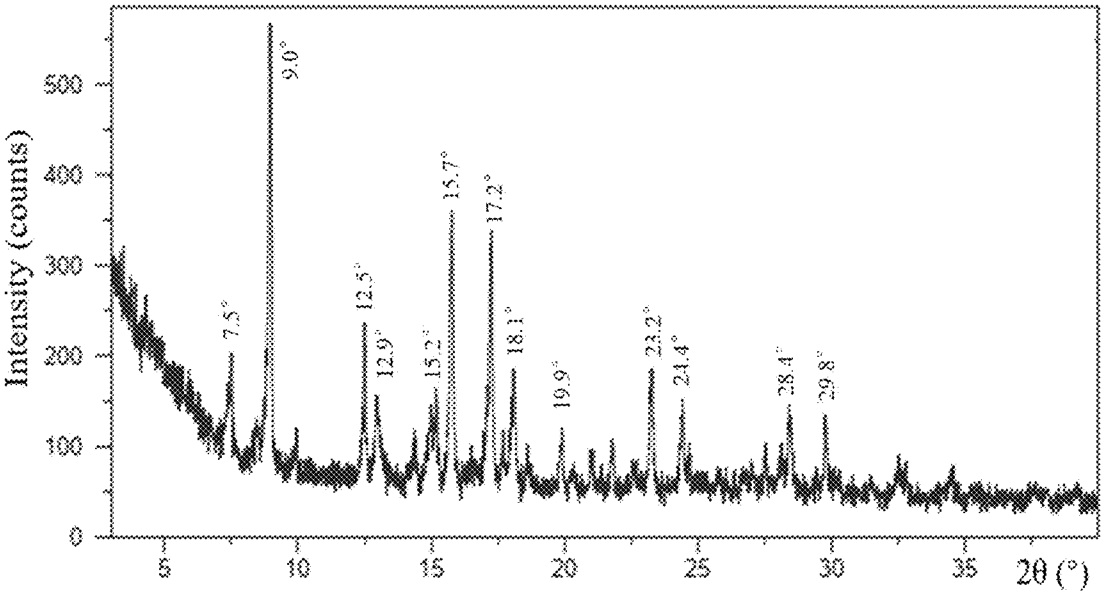
FIG. 10 shows an XRPD pattern of the anhydrous polymorph with crystalline form A of the compound of formula I.

The XRPD pattern and detailed data of the anhydrous polymorph with crystalline form A are shown in FIG. 10 and Table 8.

TABLE 8

XRPD pattern data corresponding to crystalline form A.

| No. | 2θ (°) | Relative intensity (%) |
|---|---|---|
| 1 | 3.3 | 20.5 |
| 2 | 7.5 | 20.2 |
| 3 | 9.0 | 100.0 |
| 4 | 12.5 | 31.6 |
| 5 | 12.9 | 19.2 |
| 6 | 14.4 | 8.8 |
| 7 | 15.2 | 20.0 |
| 8 | 15.7 | 64.1 |
| 9 | 17.2 | 58.6 |
| 10 | 17.7 | 11.8 |
| 11 | 18.1 | 29.0 |
| 12 | 18.6 | 6.7 |
| 13 | 19.9 | 11.1 |
| 14 | 21.0 | 6.4 |
| 15 | 21.8 | 10.7 |
| 16 | 23.2 | 28.3 |
| 17 | 24.4 | 19.0 |
| 18 | 28.4 | 16.3 |
| 19 | 29.8 | 15.7 |
| 20 | 32.6 | 4.3 |
| 21 | 34.4 | 5.0 |

Figure 11:
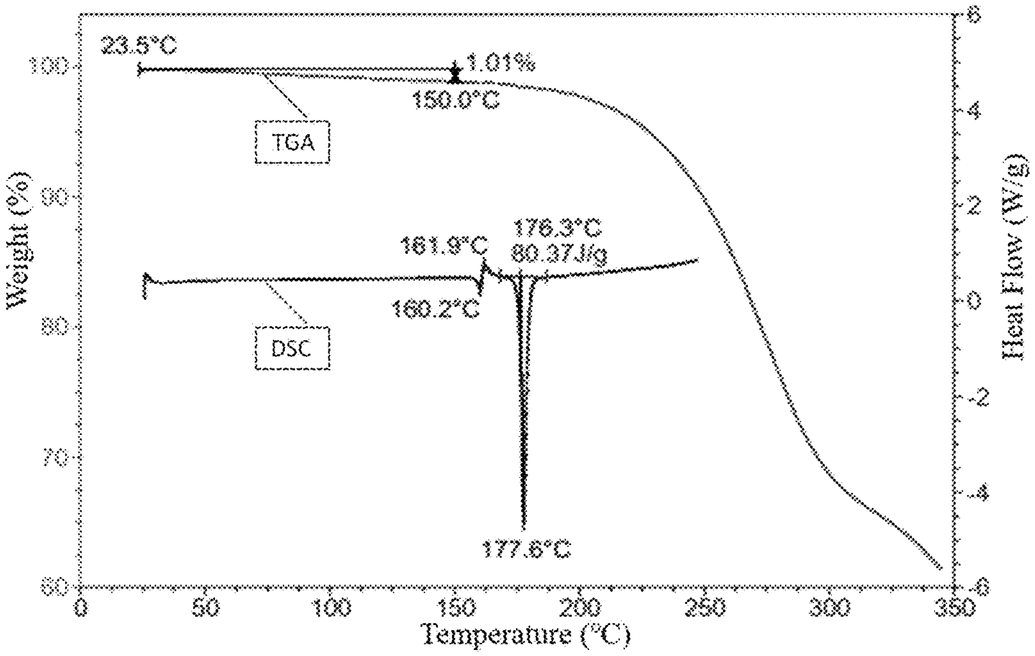
FIG. 11 shows a TGA/DSC profile of the anhydrous polymorph with crystalline form A of the compound of formula I.

The TGA/DSC profile of the anhydrous polymorph with crystalline form A were shown in FIG. 11. FIG. 11 showed that when heated to about 150.0° C., the weight loss of the sample was about 1.01%, and there was an endothermic/exothermic peak before melting at about 177.6° C. (peak temperature). According to the above data, the polymorph with crystalline form A was an anhydrous polymorph.

It was worth noting that various screening methods for solid phase transition and solution crystallization were performed, including the antisolvent addition method (a combination of methanol, acetone, tetrahydrofuran, acetonitrile, N,N-dimethylacetamide or dimethyl sulfoxide (good solvent) and water (antisolvent); a combination of methyl isobutyl ketone, ethyl acetate, 1, 4-dioxane, dichloromethane or toluene (good solvent) and n-heptane (antisolvent); a combination of isopropyl acetate. N-methyl-2-pyrrolidone, 2-methyltetrahydrofuran or chloroform (good solvent) and methyl tert-butyl ether (antisolvent)), slow volatilization method, slow cooling method, suspension stirring method (5° C./room temperature/50° C.), gas-solid infiltration method, gas-liquid infiltration method, polymer induction method and grinding method. It was found that the anhydrous polymorph with form A could be formed only by the antisolvent addition method and under the conditions of methanol/water as a good solvent/antisolvent combination.

Experimental Example 1: Thermodynamic Transition Relationships Between Polymorphs To study the thermodynamic transition relationship of the four anhydrous polymorphs (respectively corresponding to A/B/C/D), samples (each sample was about 5 mg) having crystalline forms A/B/C/D were mixed and added respectively under the conditions of 5° C./room temperature (about 20° C.)/50° C./90° C. to a saturated solution of the compound of formula I (for example, ethanol or methyl tert-butyl ether) (about 1.0 mL), and stirred (magnetic stirring, about 800 rpm), solid was separated (centrifugation, about 10000 rpm, 1 min), and XRPD test was performed.

Figure 12:
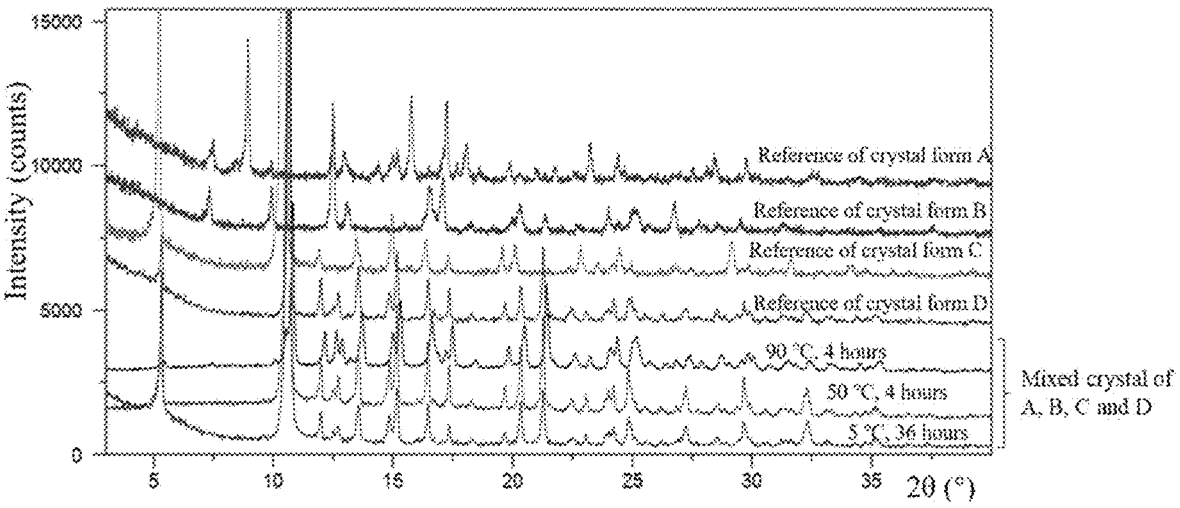
FIG. 12 shows an XRPD comparison pattern of four anhydrous polymorphs with crystalline forms A/B/C/D of the compound of formula I before and after suspension competition tests in ethanol.
Figure 13:
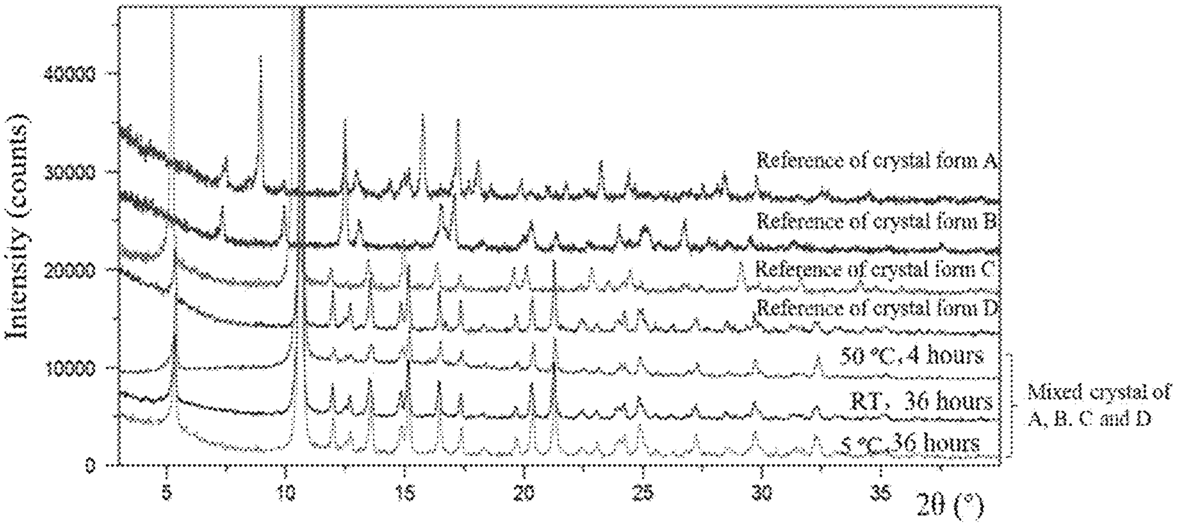
FIG. 13 shows an XRPD comparison pattern of four anhydrous polymorphs with crystalline forms A/B/C/D of the compound of formula I before and after suspension competition tests in methyl tert-butyl ether.

The results showed that at 50° C./90° C. for about 4 hours, the mixed form changed into a single form D; However, after about 36 hours at 5° C./room temperature (about 20° C.), the mixed crystalline form changed to a single crystalline form D. The XRPD detection patterns were shown in FIG. 12 and FIG. 13. The experimental results showed that the crystalline forms A/B/C can be transformed into the form D by suspension agitation under the condition of less than 90° C. In other words, the crystalline form D was more stable than the crystalline forms A/B/C at room temperature, and it was more suitable as a potential drug crystal.

In addition, it was found by the heat treatment test under nitrogen protection that crystalline form A could be transformed into crystalline form B when heated to about 160° C. and then cooled to room temperature, however, when the crystalline form C was heated to about 148° C., it can be transformed into crystalline forms B/D, further heated to about 166° C. and cooled to room temperature, all of which can be transformed into crystalline form B. In other words, crystalline form B is more stable than crystalline forms A/C under heating conditions. At the same time, the above crystal transformation phenomenon can also be confirmed by the absorption/exothermic peaks appearing in FIG. 7 and FIG. 11.

Figure 3:
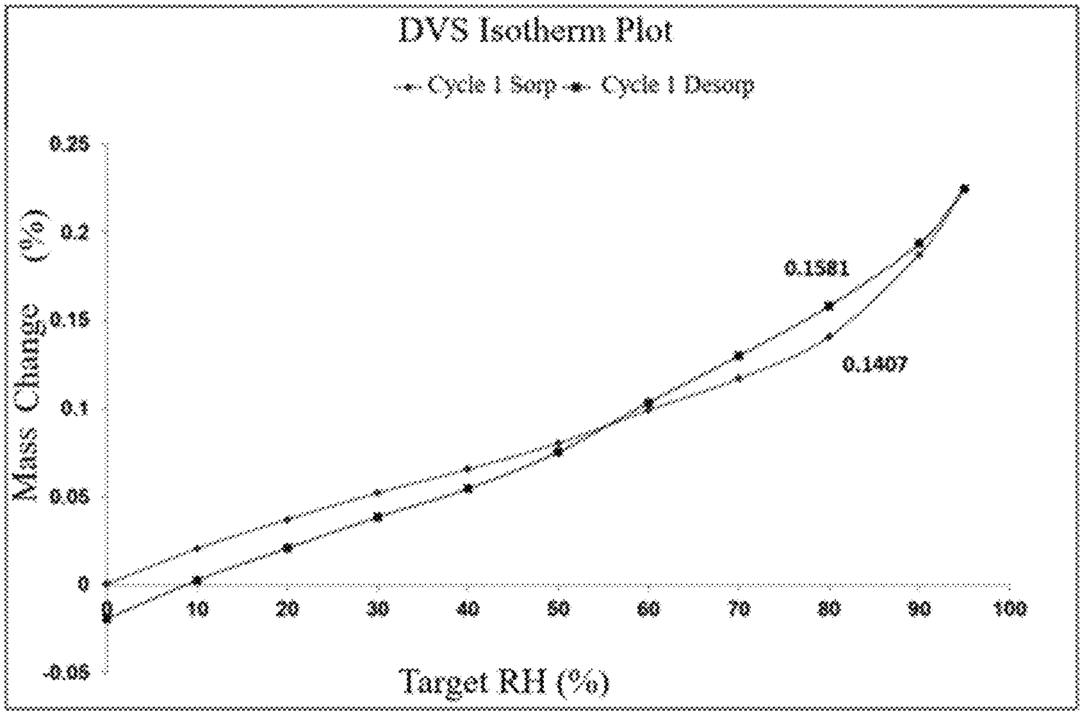
FIG. 3 shows a DVS profile of the anhydrous polymorph with crystalline form D of the compound of formula I.

Experimental Example 2: Evaluation of the Hygroscopicity of Anhydrous Polymorphs with Crystalline Form D The crystalline form D sample absorbed 0.14 wt % of water when the relative humidity was increased from 0% RH to 80% RH at a constant temperature of 25° C. (shown in FIG. 3), indicating that the crystalline form D sample had almost no hygroscopicity.

Figure 4:
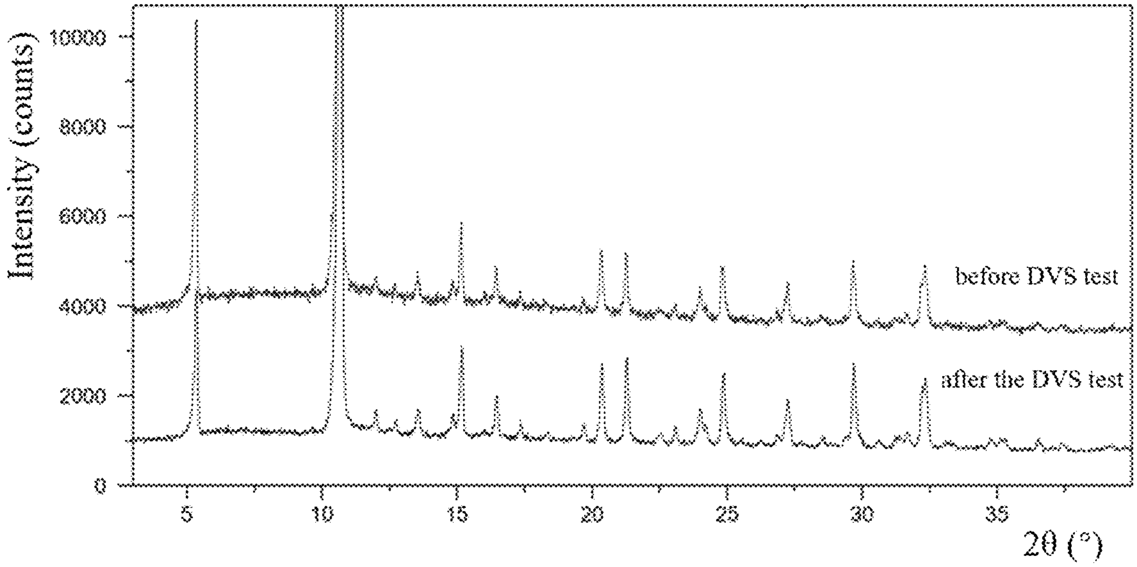
FIG. 4 shows XRPD patterns before and after DVS experiments of the anhydrous polymorph with crystalline form D of the compound of formula I.

In addition, XRPD tests were performed on the crystalline form D sample before and after the DVS experiments, and the results showed that the crystal D sample maintained the same crystalline form before and after the DVS test (as shown in FIG. 4), indicating that the crystalline form D sample not only did not have hygroscopicity but also did not undergo crystal transformation under high humidity conditions.

Experimental Example 3: Evaluation of Solid-State Stability of Anhydrous Polymorphs with Crystalline Form D To evaluate the solid-state stability of the crystalline form D samples, appropriate amounts of crystal D sample (about 10 mg) were weighed respectively, and one was allowed to stand open at 25° C./60% RH and 40° C./75% RH, and another sample of crystal D was sealed and stored at 5° C. as an evaluation control. Samples were removed after one week, and the obtained samples were characterized and tested by XRPD and HPLC to respectively detect changes in crystalline form and purity.

Figure 5:
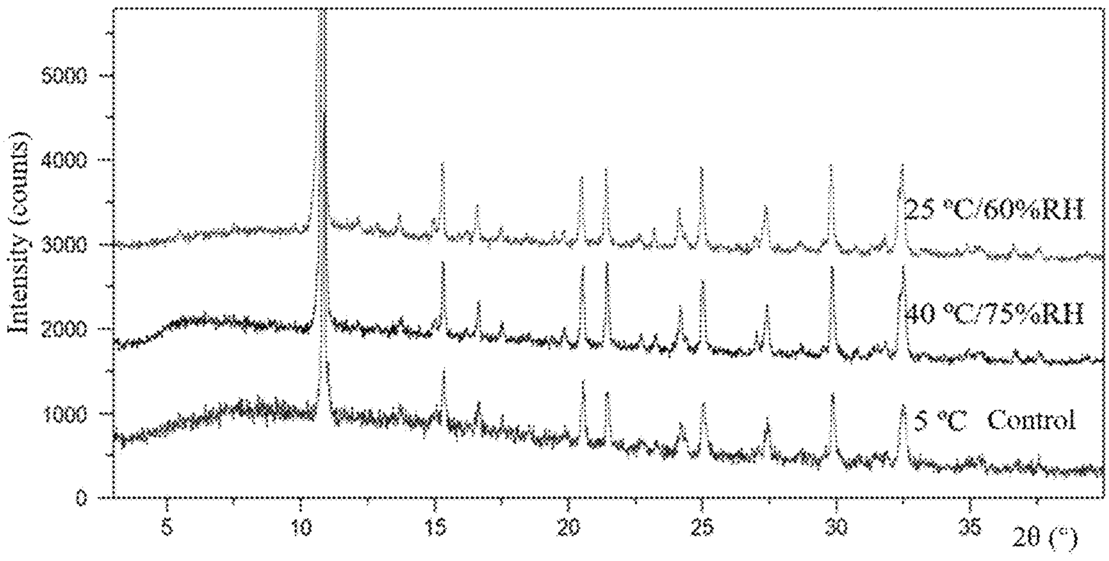
FIG. 5 shows an XRPD pattern of stability testing of the anhydrous polymorph with crystalline form D of the compound of formula I.

The XRPD pattern showed that the crystalline form D samples did not change after being placed under the corresponding conditions for one week (as shown in FIG. 5). Meanwhile, the HPLC results showed that the purity of the crystalline form D samples also did not change (as shown in Table 9). Thus, it can be seen that the anhydrous polymorph with crystalline form D of the present invention had a good physical and chemical stability.

TABLE 9

Stability test results for crystalline form D (purity tested by HPLC)

| Storage condition | Solid crystalline form after one week | Purity (Peak area %) | Relative purity (%/Control) |
|---|---|---|---|
| 25° C./60% RH, open | Crystalline form D | 99.9 | 100.0 |
| 40° C./75% RH, open | Crystalline form D | 99.9 | 100.0 |
| 5° C., sealed (control) | Crystalline form D | 99.9 | — |

Experimental Example 4: Pharmacokinetic Study

The applicant administered crystalline form D as a test drug by skin application to male and female SD rats (Sprague-Dawley rats, SD rats) respectively at a dose of 12 mg/kg; once a day for 7 consecutive days. The obtained blood concentration data were simultaneously used to calculate the relevant pharmacokinetic parameters using the pharmacokinetic processing software WinNonlin v5.2 non-atrial model for plasma pharmacokinetic characterization analysis.

The results showed that at the dose of 12 mg/kg, after 7 consecutive days of repeated administration, the ratio of AUC(0-t) of the drug on day 7 to day 1 in male and female SD rats was respectively 1.30 and 0.942. There was no obvious accumulation in male and female SD rats.

The invention claimed is:

1. An anhydrous polymorph of a compound of formula I formula I

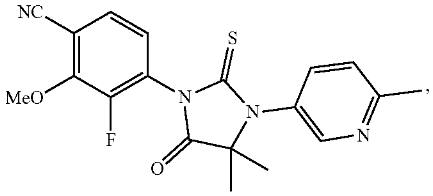

, wherein the anhydrous polymorph is a crystalline form D, wherein the crystalline form D has an XRPD pattern comprising peaks at the following 2θ angles: 5.3±0.2°, 10.7±0.2°, 13.5±0.2°, 15.1±0.2° and 21.3±0.2°.

2. A pharmaceutical composition in a solid form comprising the anhydrous polymorph according to claim 1 and a pharmaceutically acceptable excipient.

3. The anhydrous polymorph according to claim 1, wherein the crystalline form D has a TGA profile showing a weight loss of about 1.6% at 150±1° C.

4. The anhydrous polymorph according to claim 1, wherein the crystalline form D has a DSC profile showing heat absorption at 167±1° C.

* * * * *